United States Patent [19]
Chynoweth et al.

[11] Patent Number: 5,269,634
[45] Date of Patent: Dec. 14, 1993

[54] APPARATUS AND METHOD FOR SEQUENTIAL BATCH ANAEROBIC COMPOSTING OF HIGH-SOLIDS ORGANIC FEEDSTOCKS

[75] Inventors: David P. Chynoweth, Gainesville, Fla.; Robert LeGrand, Austin, Tex.

[73] Assignee: University of Florida, Gainesville, Fla.

[21] Appl. No.: 936,386

[22] Filed: Aug. 31, 1992

[51] Int. Cl.$^5$ ................................................ B09B 3/00
[52] U.S. Cl. ....................................... 405/303; 405/128; 405/129
[58] Field of Search ............... 405/52, 128, 129, 258, 405/303; 210/601, 603, 747, 170; 588/249

[56] References Cited

U.S. PATENT DOCUMENTS

| | | | |
|---|---|---|---|
| 4,269,562 | 5/1981 | Burgess | 405/129 X |
| 4,336,135 | 6/1982 | Price | 405/129 X |
| 4,396,402 | 8/1983 | Ghosh | 405/129 X |
| 4,643,111 | 2/1987 | Jones | 405/129 X |
| 4,670,148 | 6/1987 | Schneider | 210/603 |
| 4,678,582 | 7/1987 | Lavigne | 405/128 X |
| 4,844,813 | 7/1989 | Helfgott | 210/747 |
| 4,936,706 | 6/1990 | Luftenegger et al. | 405/128 |
| 5,059,066 | 10/1991 | Schindler | 405/128 X |
| 5,143,481 | 9/1992 | Schumacher et al. | 405/129 |

Primary Examiner—David H. Corbin
Attorney, Agent, or Firm—Kerkam, Stowell, Kondracki & Clarke

[57] ABSTRACT

Apparatus and method for performing sequential batch anaerobic composting on high solids content wastes are provided, wherein a plurality of longitudinally extending trenches in the ground are employed as waste-holding receptacles, each of the trenches being provided with a cover having a peripheral skirt depending downwardly therefrom to be submerged in a water-containing moat surrounding the periphery of each trench to hermetically seal the trench. The covers contain leachate sprayers and offgas recovery piping which are connected to a fixed piping system of the apparatus, and hoppers, conveyor belts and discharge plows are used to transfer the waste into the trenches, and a lifting conveyor is used to transfer the waste out of the trenches back onto the conveyor belts extending alongside the trenches. The method involves using leachate recycling in a three stage process which employs the trenches having the removable covers.

39 Claims, 11 Drawing Sheets

APPARATUS AND METHOD FOR SEQUENTIAL BATCH ANAEROBIC COMPOSTING OF HIGH-SOLIDS ORGANIC FEEDSTOCKS

BACKGROUND OF THE INVENTION

1. Field of the Invention

The present invention relates to novel methods for the anaerobic digestion of various solid waste feedstocks, including but not limited to, municipal, industrial, and agricultural wastes, biomass feedstocks including marine, woods, and grasses, and fossil feeds such as coal and peat.

2. Discussion of the Prior Art

Sanitary landfills formed by filling a land area with successive layers of solid waste, principally household waste, and layers of earth or soil are well known. The uncontrolled landfill depends upon natural biological action, precipitation and climate to effect decomposition. In areas where oxygen is present, the decomposition will be aerobic and in areas where little oxygen is present, such as at the deeper depths, decomposition will be slower and anaerobic, producing methane-containing gas. Initially, there is no methane production from the landfill and the eventual total gas production from a landfill, as compared with the total potential production, may vary widely depending upon whether the landfill has been properly designed. Total gas production can range from being extremely limited in terms of total potential gas production, to being essentially complete (i.e. close to the theoretical potential production). The formed methane is an explosion or fire hazard and may migrate to buildings or structures several hundred feet from the landfill if not removed from the landfill. Further, the natural precipitation draining out of the landfill may carry toxic contaminated water to contaminate underground water supplies, surface streams and wells. Due to the very slow stabilization, the uncontrolled landfill is not usable for other purposes for long periods of time and, thus, particularly near metropolitan areas, represents a large waste of land resources.

One approach to rendering waste disposal landfills safer is suggested by U.S. Pat. No. 3,586,624, which teaches a liquid-impervious containment of the lower portion of the landfill with continuous flow of water through the landfill to accelerate the decomposition, decrease the fire hazard and flush contaminants from the landfill in a controlled manner. The water drained from the landfill may be treated for removal of contaminants and recycled to the landfill.

In the past, methane gas has been frequently vented and flared from landfills as a safety precaution. However, in recent years and especially in view of energy conservation, the recovery and utilization of methane from sanitary landfills and the desirability of early utilization of the landfill area for other purposes has been recognized [James et al., "Methane Production, Recovery and Utilization from Landfills," Symposium Papers on Energy from Biomass and Wastes, Washington, D.C., Aug. 14-18, 1978, pages 317-324; and Stearns et al., "Recovery and Utilization of Methane Gas From a Sanitary Landfill—City of Industry, California," Symposium Papers on Energy from Biomass and Wastes, Washington, D.C., Aug. 14-18, 1978, pages 32-343]. Presently, methane is most frequently recovered from landfills by pipes extending into the landfill and transporting the methane-containing gas formed within the landfill to a collecting area for further treatment.

In the United States, millions of tons (dry) of organic wastes are generated annually in the form of municipal solid waste, agricultural residue, manure, logging and wood manufacturing residues, municipal sludge solids, industrial organic waste and miscellaneous organic waste representing production potential of trillions SCF/year of substitute natural gas (SNG). The most readily available solid waste for energy recovery is generated at about 260 million tons per year in the United States.

The biodegradable "natural" fraction of typical U.S. municipal solid waste makes up about 67% (dry or wet weight basis) of the total weight of this waste stream and is composed of approximately 41% paper, 18% yard wastes and 8% food wastes (Franklin Associates, 1988). Factors which prevent direct land disposal of this fraction are: 1) contamination with non-natural toxic or refractory components, 2) unsightly appearance in its unprocessed form, 3) production of organic acids and odors during decomposition of the rapidly biodegradable fraction, and 4) attraction of pests and spread of disease. When separated from the undesired components (hazardous wastes, plastics, metals, glass, fabrics, etc), and shredded and biologically treated to remove rapidly biodegradable components, the resulting compost product is not only suitable for land disposal, but significantly improves the water-retaining capacity of the receiving soil if the soil is light (sandy). Compost also improves aeration in heavy (clay) soils. This method of treatment provides the opportunity for integration of a major fraction of the waste stream into the natural stream for cycling of the elements in the biosphere.

The biological process applied to degradation of the rapidly biodegradable fraction of solid wastes is commonly termed "composting." Composting is normally considered to be an aerobic process accomplished either by mixing or forced aeration methods. Technically, however, the term "composting" addresses the fact that a biological stabilization process has occurred resulting in a product that has properties making it valuable as a soil amendment. The term is furthermore used most widely for treatment of feedstocks with a high solids content. It is more correct to use the term "composting" in association with anaerobic digestion when applied to conversion of high solids feeds to compost and other products [DeBaere et al., *Resources and Conservation*, Vol. 14, pages 295-308 (1987)].

Diversion of the biodegradable fraction of municipal solid waste and its treatment by composting is receiving increased attention. If potentially toxic contaminants are removed by source separation or other separation techniques, the residues of composting do not pose an environmental threat and may be disposed of, or even marketed as a compost soil conditioner. Since the biodegradable fraction composes about 67% of a typical MSW stream, any effective treatment of this fraction in a manner that diverts it from landfills will have a major impact on solving the problem of disposing of MSW.

The term "composting" is associated with either in-vessel or out-of-vessel processes in which oxygen is provided by mixing and/or by application of air to enhance decomposition. Anaerobic composting (more commonly referred to as "anaerobic digestion") accomplishes similar extents and rates of decomposition without the need for aeration or mixing (some designs). It not only has reduced energy requirements, but also produces the valuable energy product methane.

As noted previously, anaerobic decomposition in the form of a methane fermentation occurs naturally in landfills; however, decomposition is slow (requiring 5 years) and often incomplete. This slow rate may be attributed to lack of organisms, moisture and nutrients necessary for rapid fermentation. Various digester designs have been developed and tested at different scales for anaerobic composting of MSW. The more attractive options process the feedstock in its high-solids form to minimize reactor size and the possible energy penalties associated with heating water. These digester designs have included mixed, plug-flow, batch and multi-stage with leachate recycle.

Although application of anaerobic composting to high solids feeds is less developed commercially than aerobic composting, it effects equivalent conversion at similar retention times and produces a compost of equivalent quality. Capital costs of anaerobic composting are expected to be similar to those of in-vessel aerobic composting, since front and end processing operations are similar and vessel designs are not substantially different. The major advantages of anaerobic composting over aerobic composting is the lack of need for aeration or mixing and the production of a valuable fuel gas in addition to compost. For example, 100 metric tons of MSW will yield about $1,300 worth of methane (assuming $3 $GJ^{-1}$) and about $300 worth of compost (assuming $10 $ton^{-1}$ compost). This indicates that the methane credit is significantly greater than that of compost and results in an economic advantage for anaerobic over aerobic composting of about $13 per ton MSW processed. Other advantages of anaerobic composting are maintenance of nitrogen in the reduced state and lack of odors associated with partially aerobic and partially anaerobic conditions associated with outdoor aerobic composting.

Anaerobic bioconversion of the organic fraction of municipal solid waste may be considered an attractive option for inclusion in an integrated solid waste management program. The process produces a medium BTU gas without creating the air pollution problems associated with incineration. In addition, it minimizes leachate management problems and reduces the amount of solids for ultimate disposal.

Conventional mixed one-step digesters require feed material with a total solids (TS) content below 15%. However, a number of farm and municipal solid wastes have solids contents exceeding 30%. Utilizing conventional digesters could, therefore, result in a substantial volume increase compared to high-solids reactors. The main problems with low solids reactors applied to high-solids feedstocks are in the materials handling of the reactor slurry in an unmixed reactor, or prohibitive mixing energy requirements in a mixed reactor. Because of these problems, many scientists have focused their research on the development of digester designs which would effectively process high solids feedstocks.

Batch reactors may be desirable for high solids feeds because of difficulties of moving and mixing their materials. However, batch anaerobic digesters can be expected to have a high volatile fatty acid build-up in the start-up phase which leads to a drop in pH and an inhibition of methanogens. Research by a number of scientists has concentrated on overcoming these disadvantages.

Keenan [*J. Environmental Scientific Health*, All, Vols. 8 and 9, pages 525–548 (1976)], Rijkens ["A Novel Two-Step Process for the Anaerobic Digestion of Solid Waste" in Energy from Biomass and Wastes V, Symposium Papers, pages 463–475, Lake Buena Vista, Fla. (1981)], Barry-Concannon et al., [Energy From Biomass, Vol. 3 (1983)], Chynoweth et al., [Proc. 20th Intersoc. Energy Conversion Eng. Conf., pages 1.573–1.579, Miami Beach, Fla. (1985)], Smith et al., ["Biological Production of Methane from Biogas" in Methane From Biomass: A Systems Approach, pages 291–331, ed. W. H. Smith et al., Elsevier App. Sci., London (1988)], and Jewell et al., ["Engineering Design Considerations and Methane Fermentation of Energy Crop," from Annual Reports submitted to Gas Res. Inst., Chicago, Ill., Contract No. 5083-226-0848 (1983–1987)] have developed multi-stage anaerobic digesters in which the hydrolysis/acidification phase and the subsequent methanogenic phase are optimized in separate reactors and a better overall process stability is achieved. Smith and Jewell used a bench-scale leach bed/packed bed system. The leach bed batch reactor was filled with plant material such as Napiergrass, water hyacinth shoots, straw with cattle manure, or wood and, through leach bed management, the acids produced were transported to a packed bed digester and converted into biogas by a methane phase. Barry-Concannon preferred an up-flow anaerobic filter instead of a packed bed digester for the second stage.

Rijkens ["Two-Phase Process for the Anaerobic Digestion of Solid Waste; First Results of a Pilot-Scale Experiment" in Energy From Biomass, 2nd E. C. Conference Proceedings, Berlin (1982)] and Jewell scaled up their previous bench-scale designs to pilot scale. Rijkens used a 75 $m^3$ leach bed to acidify waste tomato plants and converted the acids to biogas in an up-flow anaerobic sludge blanket (UASB) reactor. Jewell scaled up the reactor to 2.4 $m^3$. They monitored five phases of digestion: 1) ensiling, 2) leaching, 3) inoculation, 4) independent operation, and 5) long-term batch operation. The leachate was converted into methane in a secondary reactor which contained partially digested sorghum removed previously from the first reactor.

Hall et al. ["Operation of Linked Percolating Packed Bed Anaerobic Digesters" in Fifth International Symposium in Anaerobic Digestion, Bologna, Italy (1988)] went one step further and used secondary and even tertiary digester reactors to produce biogas. These reactors were loaded earlier and had gone through the same phases as the newly loaded primary reactor. Leachate was percolated through a mixture of wheat straw and dairy manure in the primary digester. Subsequently, percolate was pumped into the secondary reactor and then into the tertiary, where enough methanogens had accumulated to convert the leached acids into biogas. To complete the cycle, leachate was returned back into the newest digester in order to leach out more acids and inoculate the feed with methanogens.

Having successfully demonstrated that leachate management achieves stable conversion in batch digesters filled with high solids plant biomass, Ghosh ["Solid-Phase methane Fermentation of Solid Wastes" in Eleventh American Soc. of Mech. Eng. Natl. Waste Processing Conference, Orlando, Fla. (1984)] used successfully a leach bed/packed bed concept in a bench-scale system for the breakdown of RDF (refuse-derived fuel) into biogas and stabilized residue.

Particular problems encountered in attempts to design full-scale operating units employing anaerobic composting, particularly units to be designated to handle MSW, are the sheer size requirements for providing the necessary capacity to process the MSW generated by a given municipality, and the capacity limits and operating economies of materials handling equipment required to transport and deposit the MSW in the holding cells used for composting, and to remove and transport away the compost after processing.

It is an object of the present invention to provide a novel improved apparatus and method for the anaerobic bioconversion of MSW to compost and methane.

SUMMARY OF THE INVENTION

The above and other objects are realized by the present invention, one embodiment of which provides an apparatus for performing a sequential batch anaerobic digesting or composting process for converting waste having a high-solids content to a gas phase containing methane and a solid phase comprising compost, the apparatus comprising:

a) a plurality of waste-receiving receptacles, each of the receptacles being in contact with the ground, each of said receptacles being open over a substantial portion of an upper end, b) removable cover means for covering and for substantially hermetically sealing off each of said plurality of receptacles from an external environment;

c) means carried by said removable cover means for collecting said phase comprising methane and removing said phase from each of said plurality of receptacles;

d) means carried by said removable cover means for spraying a leachate onto said waste disposed in each of said plurality of receptacles;

e) means disposed at an underside of each of said plurality of receptacles for collecting said leachate after it has percolated through said waste; and f) means for selectively transferring said collected leachate to each of said leachate spraying means in each of said plurality of receptacles.

The apparatus of the present invention for the sequential batch anaerobic composting of waste to produce a gas phase containing methane and a solid phase comprising compost may alternatively comprise:

a) a plurality of horizontally extending trenches open along an upper extent thereof;

b) at least one horizontally extending belt means disposed to the side of and extending parallel to each of said plurality of trenches for conveying waste from a predetermined end of said belt means along the entire length of each of said plurality of trenches;

c) shifting means for shifting waste from said at least one belt means to a trench adjacent to said belt means;

d) means for covering each of said plurality of trenches;

e) means for substantially hermetically sealing each of said plurality of trenches;

f) means for introducing a leachate onto waste disposed in each of said plurality of trenches to treat said waste;

g) means for draining said leachate from each of said plurality of trenches;

h) means extending between each of said plurality of trenches to at least one other of said plurality of trenches for transferring said leachate drained from each of said plurality of trenches to said introducing means of said at least one other of said plurality of trenches;

i) means for recovering said phase comprising methane from each of said plurality of trenches;

j) extraction means for extracting said waste from each of said trenches and for delivering said waste to an adjacent horizontally extending belt means for moving said treated waste to a mature compost receiving area.

A further embodiment of the invention comprises a method for the sequential batch anaerobic digestion of solid waste to produce a gas phase containing methane and a solid phase comprising compost, the method comprising:

a) in a first stage:
  i) depositing a quantity of waste to be converted into one of a plurality of open receptacles disposed in contact with the ground;
  ii) then covering said receptacle with a removable, gas-impermeable cover means;
  iii) sealing said receptacle substantially hermetically with the cover means to prevent said gas phase from escaping to an external environment and to prevent said external environment from entering said covered receptacle;
  iv) then initiating anaerobic digestion of said waste by inoculating said waste disposed in said sealed receptacle with a mature leachate obtained from a receptacle undergoing a third stage processing, said leachate containing activated culture of hydrolytic and methanogenic anaerobic microorganisms;
  v) recovering said leachate after it has passed through said waste and transferring said leachate to said receptacle undergoing said third stage processing; and b) in a second stage:
  i) continuing said anaerobic digestion of said waste to substantial completion to produce said gas and solid phases by continuously recirculating leachate passing through said waste back onto said waste in the same receptacle; and c) in a third stage:
  i) introducing a leachate recovered from a receptacle undergoing first stage processing onto said substantially completely anaerobically digested waste,
  ii) recovering said leachate after it has passed through said waste;
  iii) transferring said recovered leachate to a receptacle undergoing first stage processing;
  iv) discontinuing, after a predetermined amount of time, introduction of leachate into said receptacle, and draining the remaining leachate from said receptacle;
  v) then aerating, turning and further aerating said solid phase comprising compost;
  vi) extracting said solid phase from said receptacle; and d) in each of said first, second, and third stages in each of said plurality of receptacles, recovering said gas phase generated and transferring said gas phase to a single collection means.

DETAILED DESCRIPTION OF THE INVENTION

Sequential batch anaerobic composting (SEBAC ™) has been identified as a promising process for converting organic matter having a high solids content (>20%) to useful microbial fermentation products and compost. SEBAC ™ is a trademark/service mark of The University of Florida, the assignee of the present application, for systems which perform sequential batch anaerobic composting. Examples of high solids content organic matter which would be useful as a feedstock for this process are the aforementioned municipal solid waste (MSW), wood, industrial wastes, coal and peat. Other solid wastes which could be used as a feedstock include agricultural wastes and biomass feedstocks including marine, woods, and grasses. The description herein will focus on MSW, however it is to be understood that the invention is not to be limited to an MSW feedstock. It is a particularly important aspect of the apparatus and method of the present invention that the process does not require significant solids handling except for the filling and emptying of the trenches.

Figure 1:
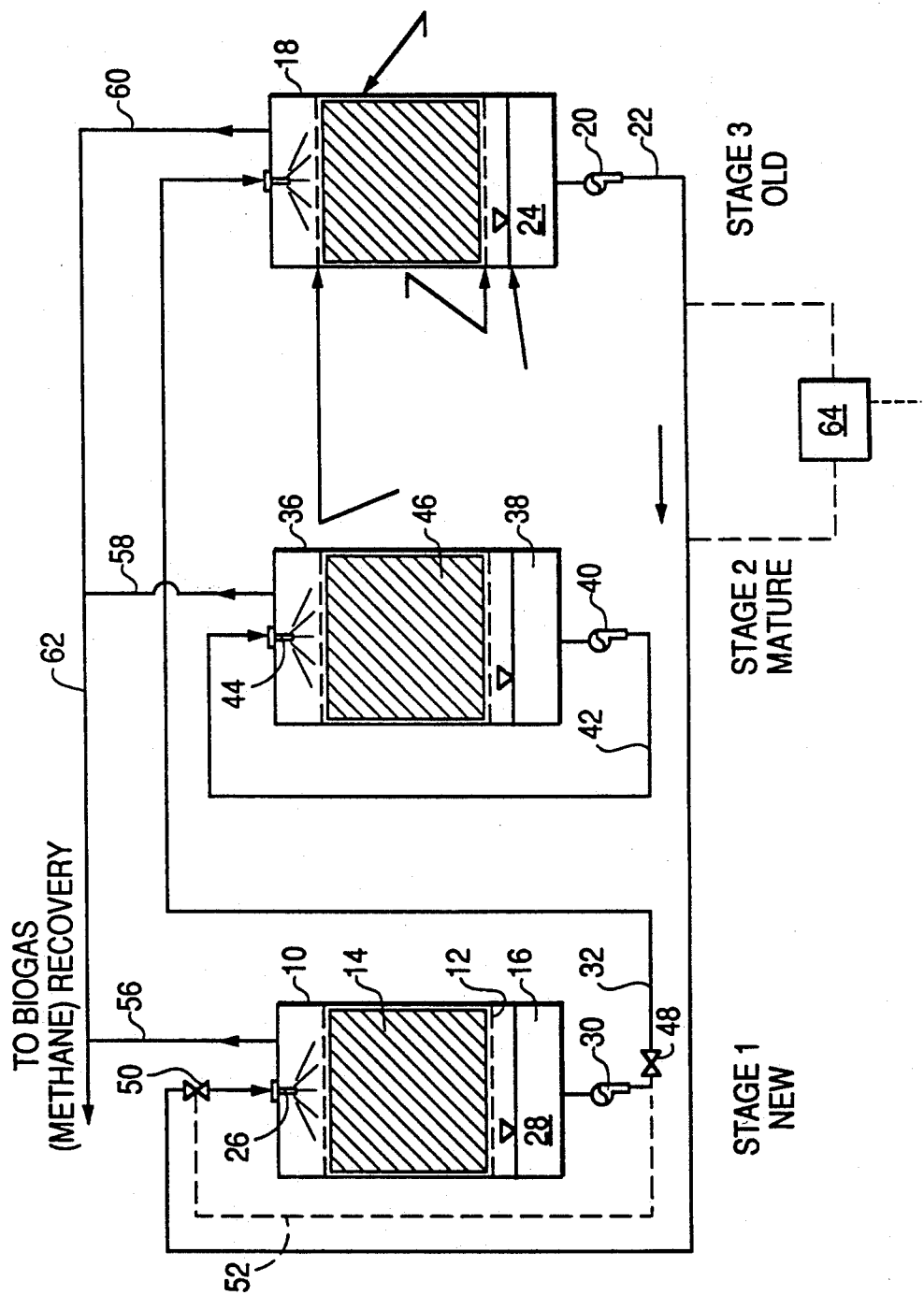
FIG. 1 is a sectional schematic view of a reactor-based sequential batch anaerobic digesting or composting system and apparatus.

FIG. 1 is a schematic view of a reactor-based pilot plant system which will be used to describe the basic operation of a sequential batch anaerobic composting process, as used to compost MSW. The biodegradable fraction of MSW, which is principally paper, yard and food waste, is coarsely shredded and placed in a reactor 10. The MSW rests on perforated plate 12 of the reactor, which separates an MSW holding zone 14 from a leachate holding zone 16.

In starting up the process, wherein, under steady state conditions, the leachate is recycled, the MSW in a first reactor, for example, reactor 10, can be heavily inoculated with leachate from another MSW-fed digester external to the instant reactor system. Once the bioconversion of MSW in reactor 10 becomes active and balanced (low levels of volatile acids), the leachate is used to start up a second reactor, which will become the "new" reactor, as reactor 10 enters its "mature" phase. The leachate is used to start up new reactors primarily to wet the feed, to carry over active microorganisms, to provide nutrients, and to remove volatile organic acids as they are formed. After the MSW in two of the reactors has reached active, balanced bioconversion, the system is ready to begin substantially steady state operation, wherein leachate from a Stage 3 reactor, in which the MSW has undergone substantially complete anaerobic digestion and bioconversion, is recycled to start up each "new" reactor coming on line to process a new batch of MSW.

Referring again to FIG. 1, it can be seen that, in steady state, or self-sustaining operation, each new batch of MSW is loaded in a reactor 10, and the MSW is moistened and inoculated with leachate which is recycled from Stage 3 reactor 18 via pump 20 and line 22. The mature leachate collected in the Stage 3 reactor contains, and is very active with respect to, the entire mixed population of microorganisms found in a balanced methane fermentation, particularly hydrolytic and methanogenic anaerobic microorganisms. The mature leachate 24 is introduced into reactor 10 by a sprayer 26 so as to allow the leachate to percolate through the mass of MSW.

As anaerobic digestion is initiated in reactor 10 by mature leachate 24, the new (percolated) leachate 28 is recycled to reactor 18 via pump 30 and line 32. The recycle of the new leachate 28 through the Stage 3 reactor achieves the removal of inhibitory fermentation products produced in Stage 1 reactor 10 by depolymerization and fermentative reactions.

In between Stages 1 (new) and 3 (old), when fermentation is established, active and balanced, each reactor is operated in a batch mode (Stage 2). In this batch mode, the leachate collected at the bottom of the reactor is reintroduced at the top of the same reactor. This is effected by providing each reactor with means for recycling the leachate to its own sprayer, as shown by reactor 36, leachate holding zone 38, pump 40, line 42, and sprayer 44, which operate to recycle the leachate onto the MSW in the MSW holding zone 46 of the reactor.

The Stage 2 batch mode operation can preferably be effected by the provision of suitable transfer lines and valving, which, in effect, convert a Stage 1 reactor to a Stage 2 reactor. As a non-limiting example, in FIG. 1, valve 48 can be shut and valve 50 can be positioned to shut off flow from line 22 and to allow flow from line 52 into sprayer 26, thus establishing a recycle means for operating in Stage 2 batch mode.

The process is preferably run such that, as one reactor enters the Stage 2 batch mode of operation, a Stage 2 reactor will have undergone a considerable amount of bioconversion and will have generated a considerable amount of methane such that it is suitable for operating as a Stage 3 reactor. By changing valve positions, the reactor can be converted from self-recycling (reactor 36) to one (reactor 18) which recycles its percolated leachate to a new Stage 1 reactor (reactor 10, FIG. 1) and which receives the percolated leachate from the new reactor into its sprayer. The process is also designed such that an existing Stage 3 reactor in which bioconversion is essentially complete can be taken off-line when a given Stage 2 reactor is converted to Stage 3 operation and when a new Stage 1 reactor is ready to be brought on line. As such, it can be seen that new reactors can continually be brought on line and old reactors in which bioconversion is complete can be taken off line and emptied, using a recycled leachate management system as just described.

FIG. 1 also shows schematically that each of the reactors 10, 18, 36, is provided with a biogas venting line 56, 58, 60, which can preferably feed into a common line or header 62 to be collected for use or further processing. In the processing of MSW according to the present invention, this biogas contains methane, which is a valuable by-product of the process. The solids are bioconverted into compost, also a useful by-product, which is emptied from the reactors after the reactors have been taken off line.

One further element shown in FIG. 1 is a toxic compound separator 64, which is tied into the leachate piping system. This separator 64 was not a part of the pilot plant which is discussed immediately below, but the inclusion of a toxic compound separator 64 is expected to be a significant enhancement to any commercial scale unit developed in accordance with the present invention. The use of inter-vessel piping systems for selectively moving the recovered leachate from one reactor to a selected second reactor in the process described above facilitates the inclusion of a toxic compound separator means 64. It has been recognized by the inventors that the leachate recovered in the reactors or other waste retaining vessels in conducting the process will carry out of the reactors toxic compounds, particularly heavy metals. The separator means 64 provides the ability to remove the heavy metals from the leachate prior to the leachate being introduced into a subsequent reactor. As a result, the compost produced by the process of the present invention will have greatly reduced levels of toxic compounds, such as heavy metals.

The separator means 64 can employ any of several known separation or removal techniques for separating the heavy metals from the leachate. Examples of suitable techniques are chemical precipitation, ion exchange, and reverse osmosis, and the use of these techniques to achieve the desired heavy metals removal will, having the benefit of the foregoing discussion, be within the level of skill in the art. If it is determined that toxic organic compounds will be present in the leachate, separation techniques such as extraction, or a suitable aerobic biological separation scheme may be appropriate for use in conjunction with, or possibly instead of, the above-mentioned techniques.

Further details of the operation of a reactor-based system for treating MSW by a sequential batch anaerobic composting process will become evident from the following example in which a pilot plant employing three reactors was run with two different MSW feedstocks. The terminology will be more process oriented than the foregoing discussion of the equipment employed in the reactor-based system.

EXAMPLE

In the following example, the following abbreviations are used:

| DRANCO | Dry anaerobic composting |
| MSW | Municipal solid waste |
| VS | Volatile solids; dry, ash-free solids |
| vvd | Volumes of methane per volume of reactor per day |

The process shown in FIG. 1 employs three stages for conversion of MSW to methane. In Stage 1 (new stage), the biodegradable fraction of MSW (mainly paper, yard waste and food waste) is coarsely shredded (to about 10 cm), placed into the reactor, and moistened and inoculated by recycling leachate from Stage 3 (old stage). Leachate recycle also removes inhibitory organics (organic acids and other fermentative products) produced in Stage 1 from depolymerization and fermentative reactions. In Stage 2 (mature stage), the fermentation is active and balanced and thus operated in the batch mode. Stage 3 (old stage) allows for completed conversion of particulates and also serves as an inoculum for the start-up of Stage 1 and conversion of acids and other fermentation products pumped out of Stage 1 via leachate.

Two sources of feedstocks were used in the reactor-based pilot plant in this example. One (referred to as Sumter Co. feed) was prepared by manual removal of aluminum, ferrous metal and some plastic from the MSW, followed by coarse shredding (2–10 cm range) with a hammermill. Fresh feed was obtained the day prior to starting each run.

A second feed (referred to as Levy Co. feed) was prepared by hand removal of the undesired components including all metal, glass, plastics and fabrics, from a municipal waste stream. The remaining fraction was coarsely shredded (2–10 cm range) with a hammermill. This feed was also obtained the day prior to starting the run.

The pilot plant system consisted of three reactors 10, 18, 36, 0.61 m in diameter×2.4 m. The middle half 14, 46 (about 0.33 m$^3$) of each reactor contained a bed of feedstock packed in nylon-mesh bags and supported underneath by a plate 12. The bags allowed for easy filling and weighing of feed and for removal and weighing of digester residues. The lower quarter of the vessel provided a place for leachate collection and storage. A leachate-recirculation system consisting of PVC pipes and perforated plate facilitated even distribution of leachate. The bed consisted of nine bags of MSW 10 containing a total of 50–100 wet kg (60–80% total solids). The typical initial bulk density for each run was about 280 g/L. The reactors were maintained at 55° C. by passing hot water through coils (not shown) wrapped around the vessel. The bioconversion process proceeds much more rapidly if the temperature is maintained at or about a thermophilic level (i.e., about 55° C.). The vessels were well insulated. Using pneumatic pumps, leachate was pumped from the bottom to the top of interconnected vessels. Thermistors (not shown) were placed in three locations in each vessel to allow for temperature measurements.

The first run was started up by heavily inoculating a bed of MSW with leachate and active solids from another MSW-fed digester. After this run became active and balanced (low levels of volatile acids), it was used to start up the second run via leachate recycle, as described above. All subsequent runs were started up from a Stage 3 reactor, as described above.

Leachate recycle was done at the same time for fifteen minutes each day, either between reactors for start-up (between Stages 1 and 3) or upon itself (Stage 2).

Runs consisted of totals of 42 or 21 days, with 14 or 7 days per stage, respectively.

Feed and effluent were analyzed for total weight and total and volatile solids. Feed composition in terms of paper, cardboard, plastic, yard waste and miscellaneous origin was determined. Gas production was measured daily using a specially designed U-tube gas meter that trips a counter every 50 mL. Gas composition was determined daily by gas chromatography. Volatile acids in leachate from the first week of Stage 1 were determined daily and from stages 2 and 3 weekly by gas chromatography. Using thermistors, temperature was determined in three different locations in all digesters daily.

RESULTS OF 42-DAY TEST

Figure 12A:
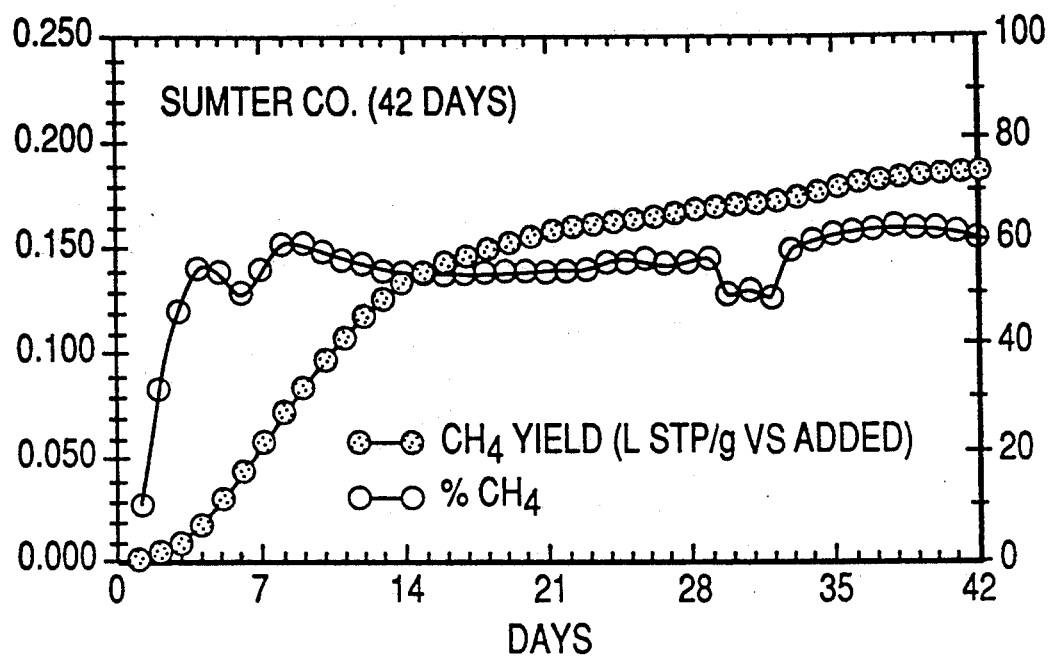
FIGS. 12A-14B are graphical depictions of performance data generated during a pilot plant run of a reactor-based system described with respect to FIG. 1.
Figure 12B:
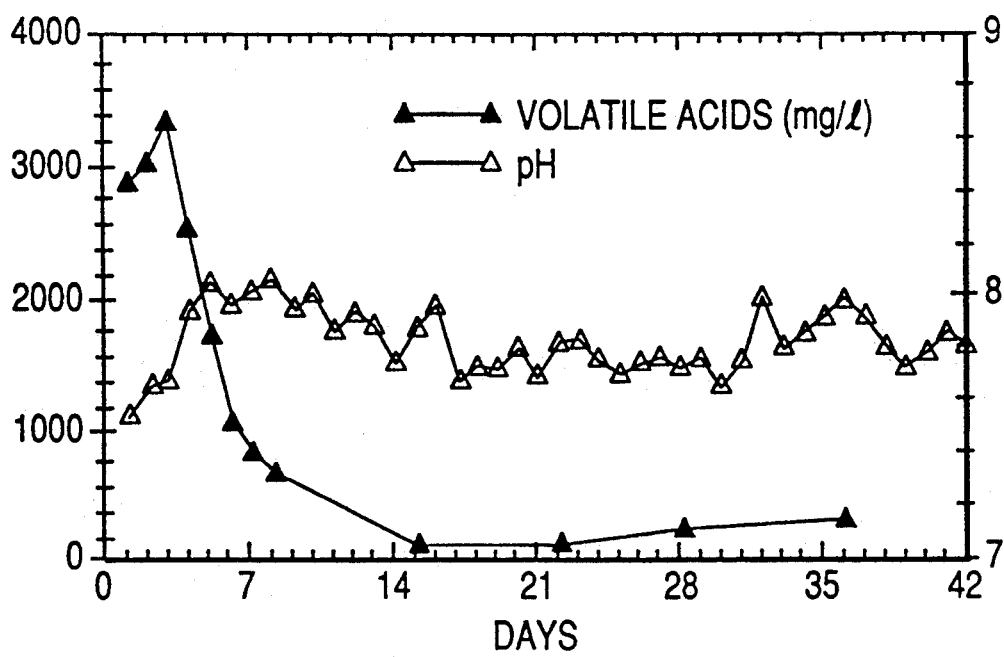

Operational parameters and performance data from four 42-day tests are shown in Tables 1 and 2, and a typical profile of performance data from a typical 42-day run is shown in FIG. 12. These tests were all conducted with Sumter Co. feedstock. During the initial part of Stage 1 (the first 14 days), over 3,000 mg/L of volatile acids accumulated and methane production was minimal. Accumulative methane yield and methane gas content rapidly increased after 5 days, indicating development of a balanced methane fermentation. During this stage, acids were carried via leachate recycle to another reactor, operating in Stage 3, where they were converted to methane and carbon dioxide. Most of the methane was produced in Stage 1. The rate of methane production leveled off in Stage 2. Methane in Stage 3 was produced in part from residual conversion of MSW and in part from volatile acids carried over from another reactor in the start-up process. The pH was in the range of 7.5-8.0, which is abnormally high for anaerobic digestion; no reason could be determined for such high pH range.

The actual loading rate for these runs was approximately 3.2 g VS $L^{-1}d^{-1}$, calculated on the basis of the bed volume, actual feed added, and residence time. Under these conditions, the mean methane yield was 0.19 L/g of VS added (range 42.4-46.0). The mean volumetric methane production rate, based on the bed volume, was 0.61 vvd. It should be recognized that the methane yield is limited by the biodegradation ability of the feed and that further degradation of this feed at longer residence times would be minimal. Loading rates and corresponding methane production rates are expected to be higher in commercial digesters because of a 55% increase in bulk density (from 176 to 272 g/L), expected in deeper Commercial systems. Another important observation is that these runs were very stable by virtue of the removal of inhibitory volatile fatty acids formed during start-up.

TABLE 1

OPERATIONAL PARAMETERS FOR TRIALS WITH A 42-DAY RETENTION TIME AND SUMTER CO. MSW

| | Trial 4 | Trial 5 | Trial 6 | Trial 7 |
|---|---|---|---|---|
| Loading Rate (g VS $L^{-1} d^{-1}$) | 3.34 | 3.17 | 3.00 | 3.12 |
| Temperature | 55° C. | 55° C. | 55° C. | 55° C. |

TABLE 1-continued

OPERATIONAL PARAMETERS FOR TRIALS WITH A 42-DAY RETENTION TIME AND SUMTER CO. MSW

| | Trial 4 | Trial 5 | Trial 6 | Trial 7 |
|---|---|---|---|---|
| Feed Characteristics: | | | | |
| Total Solids (%) | 74.1 | 70.4 | 66.1 | 80.2 |
| Volatile Solids (%) | 78.4 | 77.7 | 79.2 | 87.9 |
| Dry Composition (%): | | | | |
| Paper | 60.3 | 58.8 | 65.2 | 43.7 |
| Cardboard | 14.7 | 14.3 | 3.8 | 4.8 |
| Plastic | 7.5 | 10.9 | 12.0 | 11.2 |
| Yard Waste | — | — | — | 3.0 |
| Miscellaneous | 17.5 | 16.0 | 19.0 | 37.3 |
| Bulk Density (g/L) | 280 | 280 | 280 | 280 |

TABLE 2

PERFORMANCE DATA FOR TRIALS WITH A 42-DAY RETENTION TIME AND SUMTER CO. MSW

| | Trial 4 | Trial 5 | Trial 6 | Trial 7 | Mean |
|---|---|---|---|---|---|
| Methane Yield (L/g VS added) | 0.179 | 0.182 | 0.220 | 0.192 | 0.194 |
| Methane Production Rate (vvd) | 0.64 | 0.57 | 0.64 | 0.60 | 0.61 |
| Volatile Solids Reduction (%) | 51.0 | 48.9 | 52.4 | 46.6 | 49.7 |
| Volume Reduction (%) | 43.2 | 46.1 | 42.4 | — | 43.9 |

RESULTS OF 21-DAY TESTS

Figure 13A:
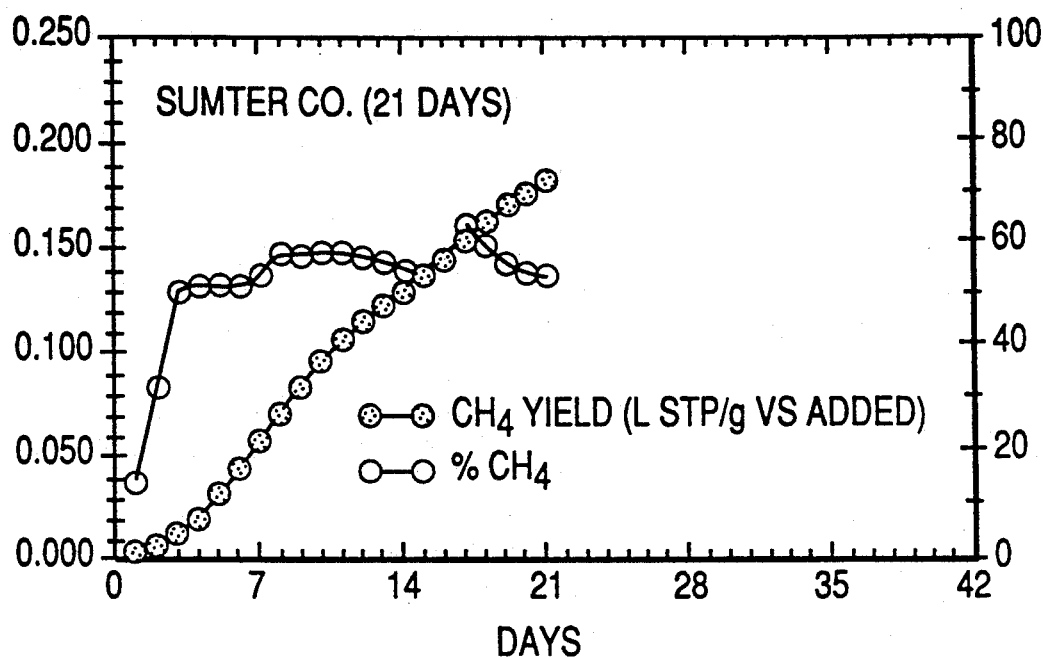
Figure 13B:
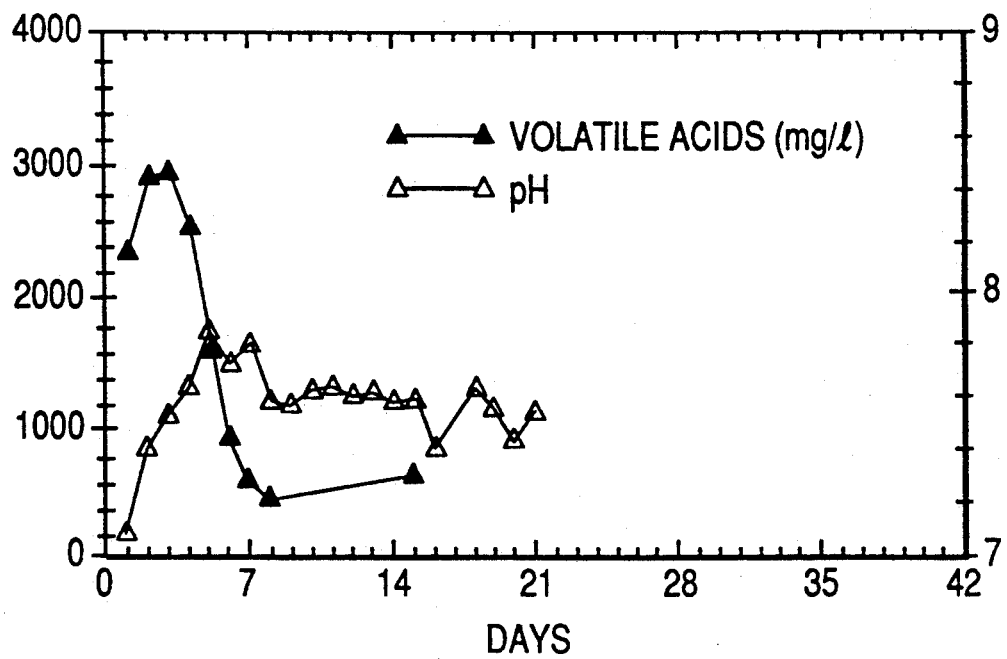
Figure 14A:
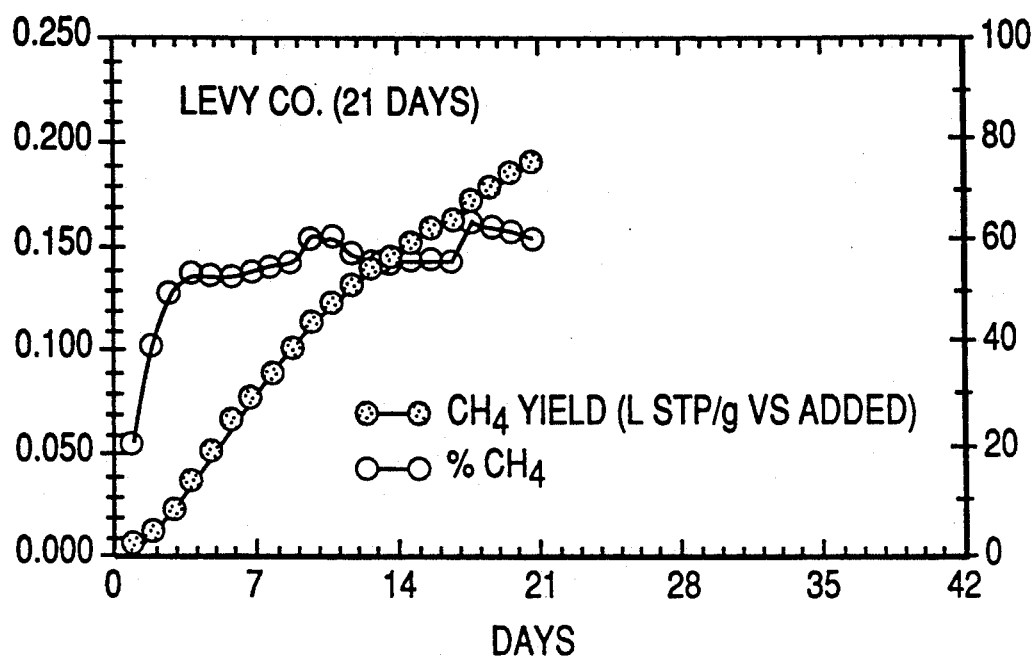
Figure 14B:
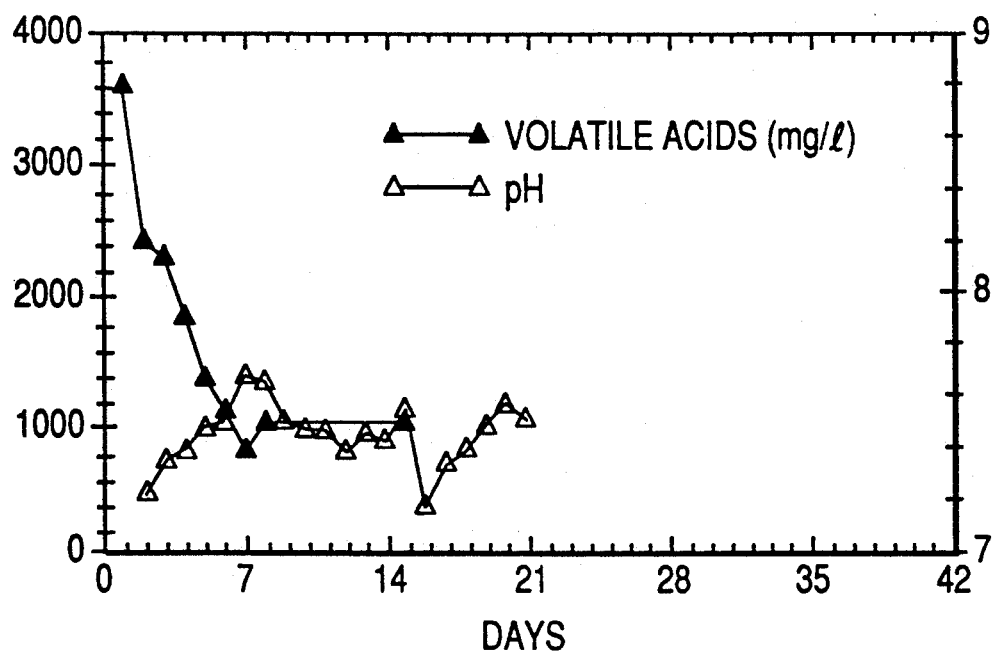

Seven tests were run With Sumter Co. feed and five With Levy Co. feed. The loading rate was about 6.4 g VS $L^{-1}d^{-1}$ for these tests, reflecting operating conditions similar to those of the above tests, except for an increased loading rate. The performance data profiles for the two feeds (FIGS. 13 and 14) follow trends similar to those of the 42-day test, except that the final level portion of the accumulative methane yield curve is excluded. Recall that each stage is 7 days instead of 14 for these runs. These plots, along with tabulated performance data below, suggest that 7 days is sufficient for adequate start-up of this system, but a total of 21 days of retention may not be enough for the desired conversion.

Tables 3-6 summarize operating parameters and performance for the 21-day tests with Sumter Co. and Levy Co. feeds. For Sumter Co. feed, the mean methane yield was 0.163 L/g of VS added (range 0.132-0.189), corresponding to a mean VS reduction of 39.7% (range 37.3-42.7). For the Levy Co. feed, the methane yield was 0.191 L/g of VS added (range 0.171-0.215), corresponding to a VS reduction range of 42.4-51.1% (three runs were continued beyond 21 days to determine ultimate biodegradation ability, and VS reduction data is not presented herein). For both feedstocks, the methane production rate was about 1 vvd. As for the 42-day runs, loading rates and corresponding methane production rates are expected to be higher in commercial digesters because of higher expected bulk densities in deeper systems. The higher methane yields and corresponding solids reductions of the Levy Co. feed are attributed to a higher fraction of biodegradable volatile solids.

TABLE 3

OPERATIONAL PARAMETERS FOR TRIALS WITH A 21-DAY RETENTION TIME AND SUMTER CO. MSW

| | Trial 8 | Trial 9 | Trial 10 | Trial 11 | Trial 12 | Trial 13 | Trial 14 |
|---|---|---|---|---|---|---|---|
| Loading Rate (g VS $L^{-1} d^{-1}$) | 6.45 | 7.54 | 6.19 | 6.98 | 5.53 | 6.68 | 5.86 |
| Temperature | 55° C. | 55° C. | 55° C. | 55° C. | 55° C. | 55° C. | 55° C. |

TABLE 3-continued

OPERATIONAL PARAMETERS FOR TRIALS WITH A 21-DAY
RETENTION TIME AND SUMTER CO. MSW

|  | Trial 8 | Trial 9 | Trial 10 | Trial 11 | Trial 12 | Trial 13 | Trial 14 |
|---|---|---|---|---|---|---|---|
| Feed Characteristics: | | | | | | | |
| Total Solids (%) | 73.4 | 56.5 | 77.0 | 67.2 | 72.9 | 73.0 | 71.1 |
| Volatile Solids (%) | 88.4 | 87.7 | 84.6 | 86.5 | 85.5 | 68.4 | 77.6 |
| Dry Composition (%): | | | | | | | |
| Paper | 57.1 | 49.3 | 38.9 | 47.6 | 55.3 | 22.0 | 25.1 |
| Cardboard | 9.2 | 8.8 | 11.8 | 29.6 | 4.2 | 14.5 | 0.0 |
| Plastic | 7.0 | 8.7 | 4.0 | 10.5 | 21.4 | 10.1 | 6.3 |
| Yard Waste | 0.0 | 0.0 | 22.7 | 0.6 | 4.6 | 7.5 | 2.0 |
| Miscellaneous | 26.7 | 33.5 | 22.6 | 11.7 | 14.5 | 46.0 | 66.7 |
| Bulk Density (g/L) | 280 | 280 | 280 | 280 | 280 | 280 | 280 |

TABLE 4

PERFORMANCE DATA FOR TRIALS WITH A 21-DAY
RETENTION TIME AND SUMTER CO. MSW

|  | Trial 8 | Trial 9 | Trial 10 | Trial 11 | Trial 12 | Trial 13 | Trial 14 | Mean |
|---|---|---|---|---|---|---|---|---|
| Methane Yield (L/g VS added) | 0.132 | 0.171 | 0.137 | 0.181 | 0.151 | 0.182 | 0.189 | 0.163 |
| Methane Production Rate (vvd) | 0.84 | 1.27 | 0.85 | 1.26 | 0.82 | 1.21 | 0.87 | 1.02 |
| Volatile Solids Reduction (%) | — | — | — | 41.4 | 44.4 | 37.0 | 21.1 | 36.0 |
| Volume Reduction (%) | 42.7 | 40.0 | 38.9 | — | 37.3 | — | — | 39.7 |

TABLE 5

OPERATIONAL PARAMETERS FOR TRIALS WITH A
21-DAY RETENTION TIME AND LEVY CO. MSW

|  | Trial 15 | Trial 16 | Trial 17 | Trial 18 | Trial 19 |
|---|---|---|---|---|---|
| Loading Rate (g L$^{-1}$ d$^{-1}$) | 5.07 | 5.27 | 5.24 | 6.28 | 6.94 |
| Temperature | 55° C. | 55° C. | 55° C. | 55° C. | 55° C. |
| Feed Characteristics: | | | | | |
| Total Solids (%) | 62.0 | 72.5 | 67.2 | 64.3 | 62.1 |
| Volatile Solids (%) | 92.5 | 94.1 | 91.0 | 95.3 | 89.5 |
| Dry Composition (%): | | | | | |
| Paper | 85.0 | 91.3 | 95.9 | 98.5 | 87.0 |
| Cardboard | 7.0 | 7.0 | 3.2 | 0.4 | 2.8 |
| Plastic | 0.8 | 0.0 | 0.9 | 0.0 | 0.0 |
| Yard Waste | 0.0 | 1.6 | 0.0 | 1.1 | 8.4 |
| Miscellaneous | 7.2 | 1.8 | 0.0 | 0.0 | 1.8 |
| Bulk Density (g/L) | 280 | 280 | 280 | 280 | 280 |

TABLE 6

PERFORMANCE DATA FOR TRIALS WITH A 21-DAY
RETENTION TIME AND LEVY CO. MSW

|  | Trial 15 | Trial 16 | Trial 17 | Trial 18 | Trial 19 | Mean |
|---|---|---|---|---|---|---|
| Methane Yield (L/g VS added) | 0.199 | 0.188 | 0.171 | 0.182 | 0.215 | 0.191 |
| Methane Production Rate (vvd) | 1.00 | 1.00 | 1.03 | 1.13 | 1.13 | 1.06 |
| Volatile Solid Reduction (%) | 36.7 | 44.6 | runs were continued beyond test period | | | |
| Volume Reduction (%) | 42.4 | 51.1 | runs were continued beyond test period | | | |

The pilot plant runs are indicative that sequential batch anaerobic composting is effective for conversion of the biodegradable fraction of MSW to methane. Compared to other processes described for anaerobic digestion of MSW (Table 7) methane yields were similar, but are more a reflection of the ability of the feedstock to be biodegraded than of process-specific factors. The significantly higher loading rates and associated higher methane production rates reported for DRANCO (12) and VALORGA (13) reflect the lower residence times and higher bulk densities employed in these designs. It should be pointed out that values for loading rate and methane production rate for the SEBAC process would be expected to be higher in a commercial system in consequence of higher bulk densities expected in larger reactors. A comparison of these systems must also take into account other factors such as simplicity of design and operation, process stability, energy requirements and overall process economics.

TABLE 7

REACTOR PERFORMANCE COMPARISON
FOR ANAEROBIC DIGESTION OF MSW (RDF)

| Reactor | RefCoM CSRT (14) | SOLCON (15) | DRANCO (12) | VALORGA Mixed (13) | GOSH LBAFR (6) | SEBAC* 42 Days Sumter MSW | SEBAC* 21 Days Sumter MSW | SEBAC* 21 Days Levy MSW |
|---|---|---|---|---|---|---|---|---|
| Temperature (°C.) | 60 | 35 | 50 | 37 | 35 | 55 | 55 | 55 |
| Loading (g VS L$^{-1}$ d$^{-1}$) | 3.0–9.6 | 3.2 | 16 | 15 | 1.1 | 3.2 | 6.4 | 6.4 |
| Retention Time (d) | 6–27 | 18 | 20 | 15 | 90 | 42 | 21 | 21 |

TABLE 7-continued
REACTOR PERFORMANCE COMPARISON FOR ANAEROBIC DIGESTION OF MSW (RDF)

| Reactor | RefCoM CSRT (14) | SOLCON (15) | DRANCO (12) | VALORGA Mixed (13) | GOSH LBAFR (6) | SEBAC* 42 Days Sumter MSW | SEBAC* 21 Days Sumter MSW | SEBAC* 21 Days Levy MSW |
|---|---|---|---|---|---|---|---|---|
| Methane Yield (L/g VS added) | 0.13–0.30 | 0.25 | 0.28 | 0.20 | 0.21 | 0.18–0.22 | 0.13–0.19 | 0.17–0.22 |
| Methane Rate (vvd) | 0.39–2.9 | 0.80 | 4.4 | 3.0 | 0.24 | 0.5 | 1.0 | 1.0 |

*This study

As noted previously, substantial problems are encountered in attempting to design commercial scale equipment and systems for sequential batch anaerobic composting. Particular problem areas to be addressed include ensuring that the operation of the apparatus will be capable of being economically competitive with other forms of waste disposal, designing a materials handling system capable of loading and unloading the waste in sufficiently short times, and limiting, to the extent possible, the overall size of the apparatus for a given waste throughput capacity, as the sheer size of a system designed to handle MSW from a large municipality can dictate whether the system will be economically competitive with other waste disposal systems.

As an example, simply scaling up the reactor-based pilot plant is unlikely to yield a commercially viable design for a system, given that the means by which the reactor vessels would be loaded and unloaded would have to be quite complex and expensive, and would be slow in operation.

The apparatus and system depicted substantially schematically in FIGS. 2–11 are preferred embodiments of an apparatus in accordance with the present invention which is particularly well suited for commercial scale operation of a sequential batch anaerobic composting process.

Figure 2:
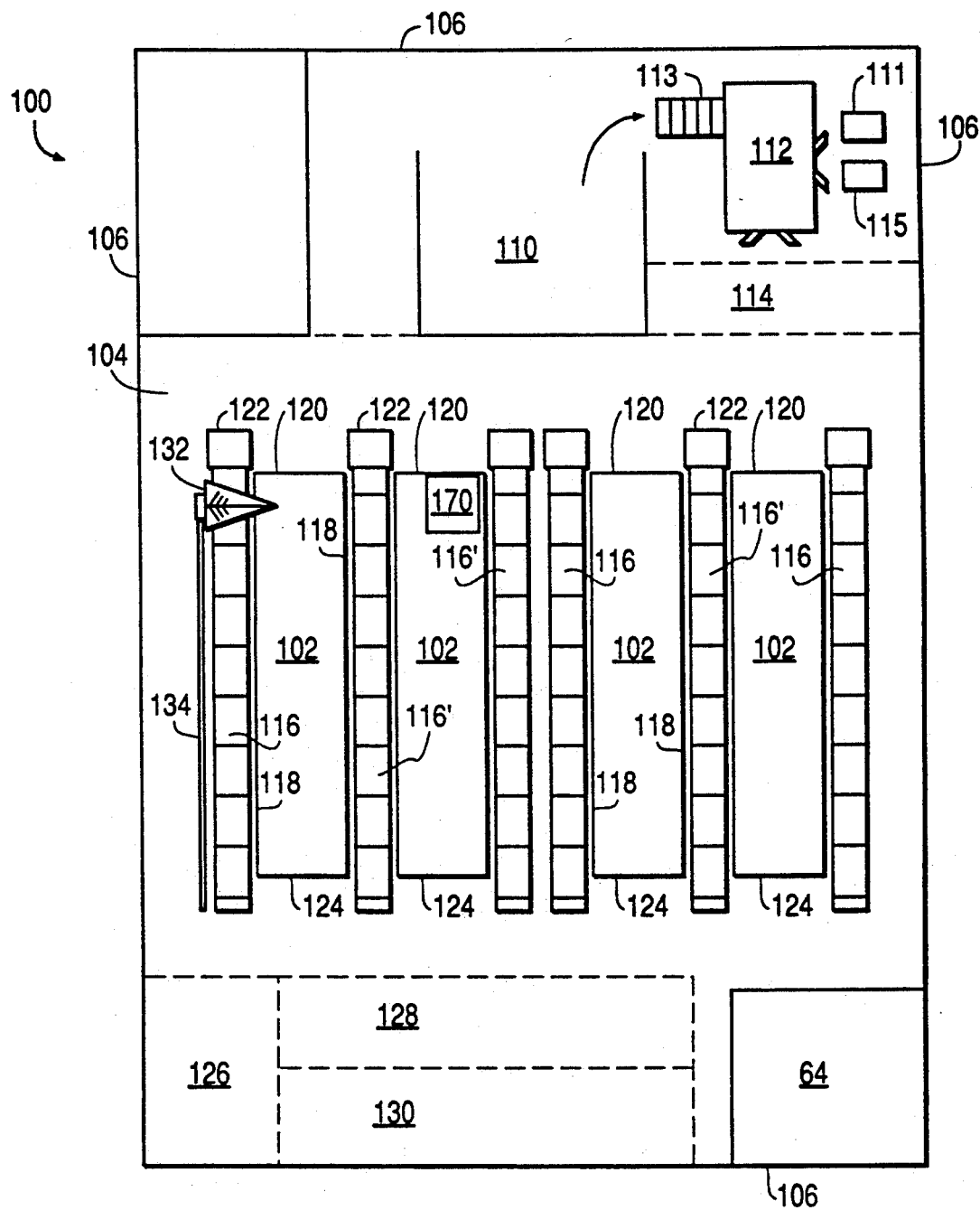
FIG. 2 is a schematic top plan view of an apparatus for sequential batch anaerobic composting in accordance with a preferred embodiment of the present invention.
Figure 3:
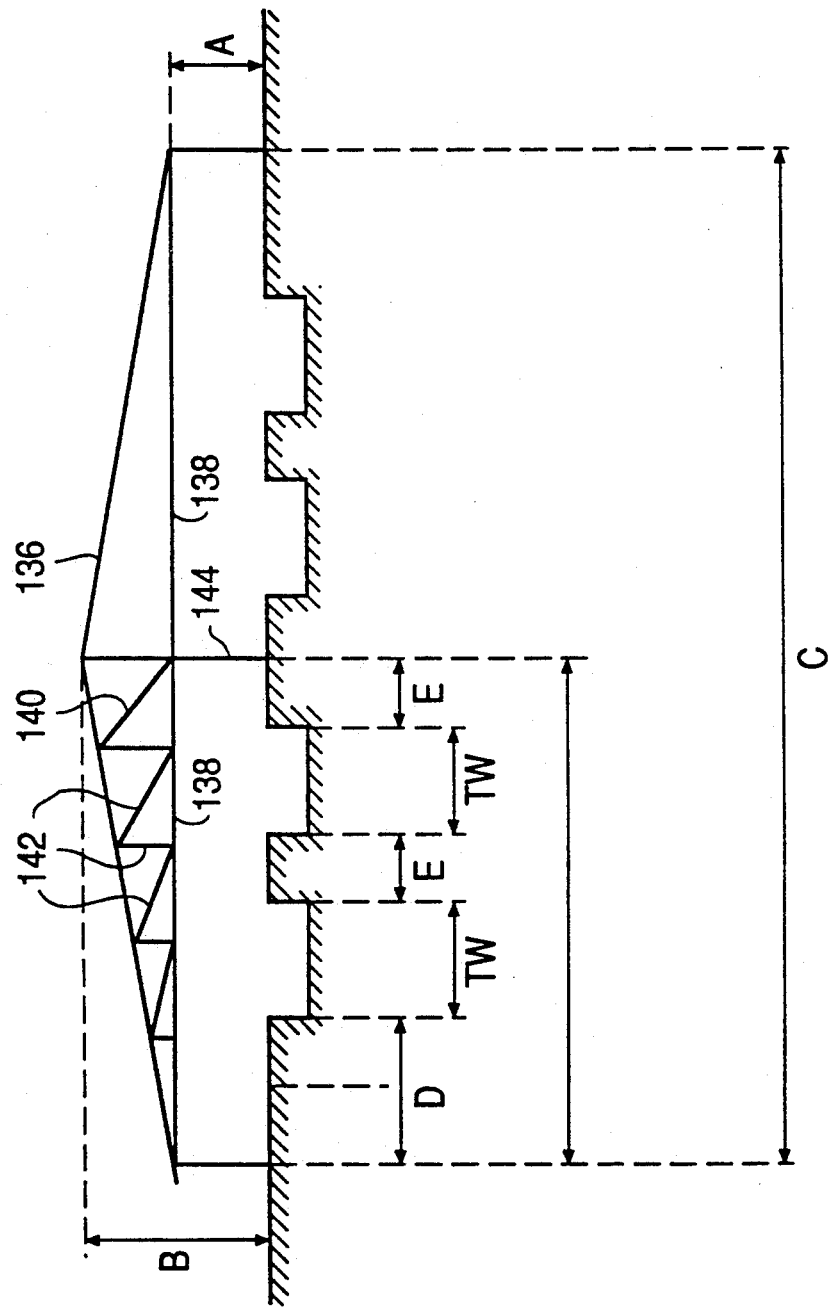
FIG. 3 is a schematic cross-sectional view of the apparatus of the preferred embodiment.

Referring initially to FIGS. 2 and 3, an apparatus 100 is illustrated in substantially schematic form wherein the principal feature is the provision of a plurality (four shown) of waste-receiving receptacles, depicted as longitudinally extending trenches 102, preferably disposed in the ground, which serve as the MSW holding zones for the system. The construction of the trenches will be described in further detail later in this description. Although four trenches are shown in FIG. 2, it may be possible to operate the apparatus in the manner described with respect to the FIG. 1 process with as few as three trenches. However, from the standpoint of operating the system in an economically competitive manner, four trenches is likely to be a practical minimum, and a system having five or more trenches is likely to be the most economically operated system.

One factor in selecting the number of trenches is that the gas (methane) produced in the process will desirably have a further use, either being sold or used to generate power. In either event, a certain minimum delivery must be guaranteed. However, the present process inherently has "peaks and valleys" of gas production, as opposed to having a more desirable constant gas production. In general, as the number of trenches is increased, the amplitude of the fluctuations (height of peaks and valleys) diminishes, thereby improving the consistency of the gas production.

A further factor in the economics of operating the apparatus of the present invention is the staffing and tasking at the facility. Operations should preferably be scheduled during normal working hours (Monday–Friday, 8 a.m.–5 p.m.) because, in this process context, evening and weekend work will likely be unaffordable except for minimal monitoring of the facility. In order to ensure reliable operation, the scheduling of tasks should be as simple as possible. The various tasks or suboperations would thus be done on a repeating weekly schedule, i.e., on Mondays, task or operation "A" is performed, on Tuesdays, task or operation "B" is performed, and so on.

In an MSW digesting facility, it is expected that garbage will be brought in every weekday, and the garbage must obviously be put somewhere. Logically, the incoming garbage would be deposited in the trenches. In order to minimize the development of odors and unsanitary working conditions, the filling of a given trench should not extend past one week's time.

One preferred scenario of operation would have a selected trench, which has completed the digesting process, rapidly emptied as a first task on a Monday morning. This trench is then immediately put back in service, receiving incoming garbage, and the filling of the trench continues through midday Friday, with approximately four-plus days having elapsed for the emptying-filling operation. The trench may then be covered to begin the anaerobic digestion process.

A cycle time will be defined as the time elapsed between one filling of the trench and the next filling of the trench. Since trench filling is scheduled to commence on Mondays following trench emptying, it can be seen that the cycle time should be a multiple of seven days. An anaerobic residence time will be defined as the cycle time minus eight days, as four days are taken up in filling the trench, and it is desirable to have approximately four days of aerobic operation at the end of the anaerobic processing. Pilot plant work suggests that the anaerobic residence time must be a minimum of 21 days to ensure a sufficient conversion efficiency. The resulting cycle time would thus be the 21 days of anaerobic residence time plus the eight days for filling and subsequent aerobic operation, for a total of 29 days, or one day more than four weeks. With the object or process constraint that one trench be filled every week, five trenches are thus desired, whereas, if four trenches are used, the cycle must be held to 28 days, thus shortening by one day the anaerobic residence time and jeopardizing conversion efficiency.

About the only feasible way of operating under the above process constraints with three trenches would be to operate on a 42-day cycle time, using two weeks as the filling time for a given trench. While this system would achieve several of the benefits of the process of the present invention, it has the probable disadvantages of leading to excess odor generation and creation of unsanitary work conditions.

The apparatus is preferably contained in a building structure 104 bounded by walls 106 and a roof 138 (FIGS. 3, 5, 6), which provides the ability to contain odors generated in the anaerobic composting process, and which maintains a more attractive appearance at the site, as compared with, for example, open landfills. The building will also protect the trench covers (described later) against precipitation, wind, ultraviolet radiation, and birds. The building further provides a structure which is advantageously used as part of the trench cover raising and lowering system.

The building 104 preferably is equipped with a tipping floor 110, onto which garbage trucks can deliver the MSW collected by the trucks at transfer stations or from individual routes. A materials recovery facility 112 of conventional construction is provided adjacent the tipping floor, wherein the MSW can be sorted to remove recyclable materials and reject materials, and can be shredded. The resulting material is termed refuse derived feed (RDF), and an RDF storage area 114 is provided adjacent to the materials recovery facility, which effectively serves as an accumulator zone for storing up to two days worth of production from the materials recovery facility. Transfer of MSW from the tipping floor 110 to the materials recovery facility 112 and from facility 112 to the RDF storage area 114 can be accomplished by front end loader, or comparable material-moving equipment. Alternatively, the in-house materials recovery facility can be omitted, and output from an existing materials recovery facility could be used as the feedstock.

In the depicted preferred embodiment, each of the trenches 102 has a conveyor belt means 116, of the endless belt type, extending along each side 118 of the trench. At a front end 120 of the trench, loading hoppers 122 are provided for each of the conveyor belts. The conveyor belts extend along the entire length of the trenches 102, terminating at positions beyond the back ends 124 of the trenches. The conveyor belts are thus adapted to carry the RDF along the entire length of the trenches, facilitating the filling of the entire trench with RDF for the anaerobic composting process, and facilitating transport of the composted material to its final processing areas. The RDF is transported by a front end loader from the RDF storage area 114, and loaded into the hoppers 122 by a front end loader, or a crane/clamshell device, and the hopper regulates the feeding of the RDF to each conveyor belt 116.

The final processing areas shown schematically in FIG. 2 are a screening area 126 used to separate out material which is too large to be used in the final, salable compost product. The smaller material not separated in the screening process is moved into one of two static pile areas 128, 130, for final treatment prior to removal as a mature compost product. The transport of the composted material from the back ends 124 of the conveyor belts to the screening areas 126 and to the static pile areas 128, 130, may also be accomplished by front end loaders or other comparable material-moving equipment. Also disposed in the building at an appropriate location is the toxic compound separator means 64.

One final element depicted in FIG. 2 is a discharge plow 132, disposed to overhang the conveyor belt 116, and which is used to scrape the RDF off of the conveyor belt 116 into the adjacent trench 102 to fill the trench for anaerobic batch composting. Each conveyor belt 116 in the depicted embodiment will have at least one discharge plow associated therewith. It will be noted that the discharge plow or plows associated with the conveyor belts 116' positioned to service two adjacent trenches will be required to be capable of scraping the RDF into either of the trenches 102, as desired. The discharge plows (one shown in FIG. 2) have means for moving the plow 132 along substantially the entire length of the trench 102. A track 134 can be provided for each plow, and the plows can be driven by motorized wheels or by a belt along such a track, for example.

It is contemplated that other means for moving the RDF from the conveyor belt into the trenches could be employed with substantially equal effectiveness. An example of an alternate conveyor-emptying means would be a tripper adapted to dump the material from the belt into the trench.

FIGS. 3–7 schematically illustrate further constructional details of the building 104 and the elements associated with the trench in this preferred embodiment of the invention. The schematic cross-section of FIG. 3 is provided to show some of the dimensions of a high capacity commercial scale apparatus constructed in accordance with the present invention. The height of the building walls 106, represented by dimension A in FIG. 3 may be on the order of twenty (20) feet. The height B of roof 108 may be on the order of forty (40) feet. This figure also depicts, in schematic form, the construction of the roof, which can be a simple construction such as an outer weather resistant covering 136 and an inner ceiling layer 138 surrounding a support structure 140 made up of a plurality of interconnected struts 142 and a central support post 144. The total width C of the building having the four trenches as depicted can be on the order of 206 feet, with each trench having a width TW of 24 feet, and with the outer trench spacing D from wall 106 being 29 feet. The spacing E between adjacent trenches in this configuration would be on the order of 13 feet.

Figure 4:
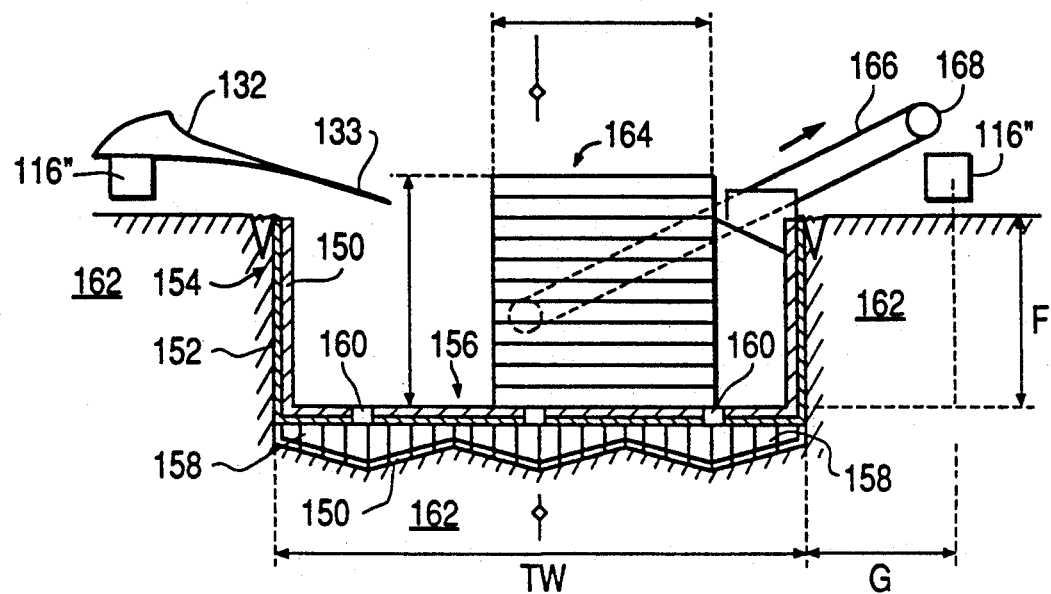
FIG. 4 is a substantially schematic cross-sectional view of a trench employed in the apparatus of the present invention, the cross-section being taken transverse to a longitudinal axis of the trench.

The construction of the trench 102 is set forth in further detail in the cross-section view of FIG. 4. The trench 102 preferably has a concrete liner 150, and, optionally, an additional thermal insulation layer 152, covering side walls 154 and forming a bottom wall 156 of the trench. Extending underneath the bottom wall 156 is a leachate collection drain system 158 into which the leachate percolated through the RDF flows via openings 160 in the concrete bottom wall of the trench. The drain 158 may also be lined with a concrete liner 150, and the drain will have means for routing leachate collected therein to a withdrawal line.

As noted previously, a preferred trench width TW is 24 feet. As shown in FIG. 4, the depth F of the trench 102 is a relatively shallow ten (10) feet. The depth F of the trench in a commercial scale apparatus should be minimized to the maximum extent practical, in order to avoid problems with permeability limitations involving the leachate.

The positions of conveyor belts 116 relative to the trench 102 are shown schematically by boxes 116'', and a centerline of the belt is spaced from the sidewall of the trench at a distance G of six feet, six inches (6'6''). Discharge plow 132 is shown as being positioned above the left side conveyor belt 116'', and it can be seen that the distal end 133 of the plow blade extends to a position approximately one-quarter of the width TW of the trench 102. It can also be seen that the position of the portion of the plow overhanging the trench is higher than the upper edge, so that the plow is capable of filling the entire height of the trench 102 with the RDF.

Also depicted in FIG. 4 is a schematic representation of a windrow turner 164 equipped with a lifting discharge conveyor belt 166 oriented transversely to the longitudinal extent of the trench. The windrow turner can be of conventional design, such as the SCAT Windrow Turner Model 4833, and such devices are well known in the art. The lifting conveyor 166, being of the endless belt type and powered in a conventional manner, is attached to the windrow turner 164 in a position to receive the composted RDF being lifted and turned by the windrow turner in the trench 102, is angled upwardly and pointed toward the side of the trench, and extends over to a position wherein its discharge end 168 is located over one of the longitudinally extending conveyor belts 116'' extending along the side of trench 102.

The windrow turner 164 is adapted to travel along the longitudinal extent of the trench 102, and may be used to turn the composting material at one or more predetermined times during the process, and the turner 164 is used in conjunction with the lifting conveyor 166 to remove the material from the trench after that particular trench has completed Stage 3 (FIG. 1) processing. The turner generally extends across approximately one-half of the width of the trench, thereby enabling the turner to mix the material in the trench or to empty the trench in two passes in the trench. The longitudinal conveyor 116 is used to transport the processed material past the back end 124 (FIG. 2) of the trench, and to dump the material off of the end of the belt in proximity to final processing areas 126, 128, 130 (FIG. 2). The windrow turner is capable of servicing more than one, and potentially all, of the trenches 102 of the apparatus 100, assuming that the number of trenches is relatively low, as the windrow turner 164 is lowered into each trench by an hydraulic elevator 170 (FIGS. 2, 6) disposed in the trench 102 adjacent the front end 120 thereof. After the windrow turner has completed its task in a given trench, the hydraulic elevator can be used to raise the turner up to the level of the top of the trench, and the turner can be driven to a wait station or directly to another trench, as desired.

Figure 5:
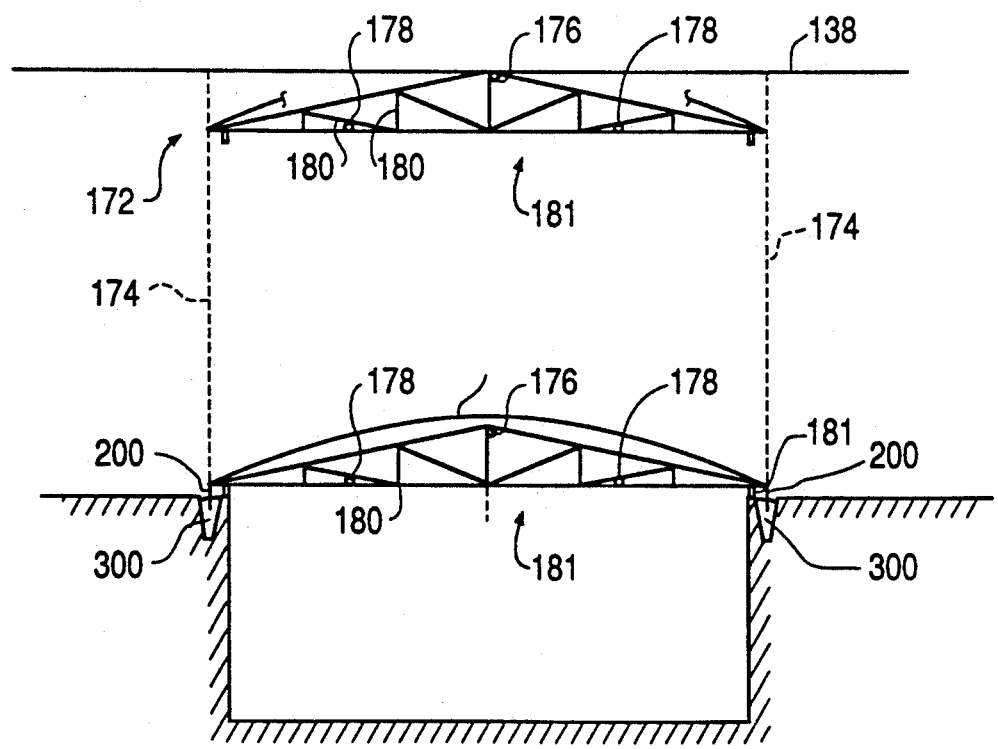
FIG. 5 is a substantially schematic cross-sectional view of a trench and trench cover, the cross-section being taken transverse to a longitudinal axis of the trench.
Figure 6:
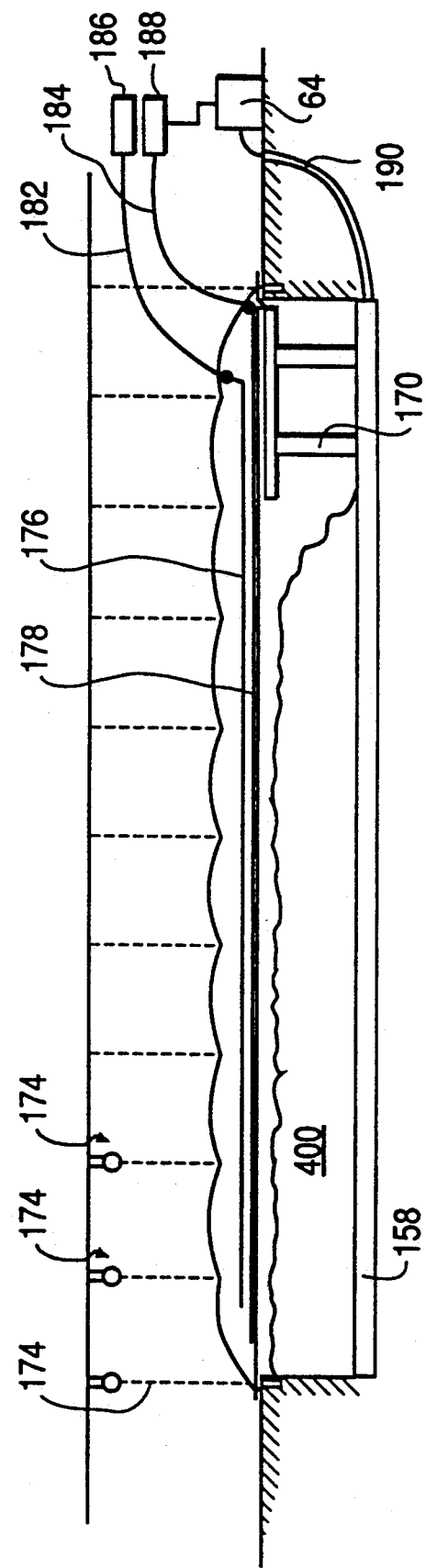
FIG. 6 is a substantially schematic cross-sectional view of the trench and trench cover employed in this preferred embodiment.
Figure 7:
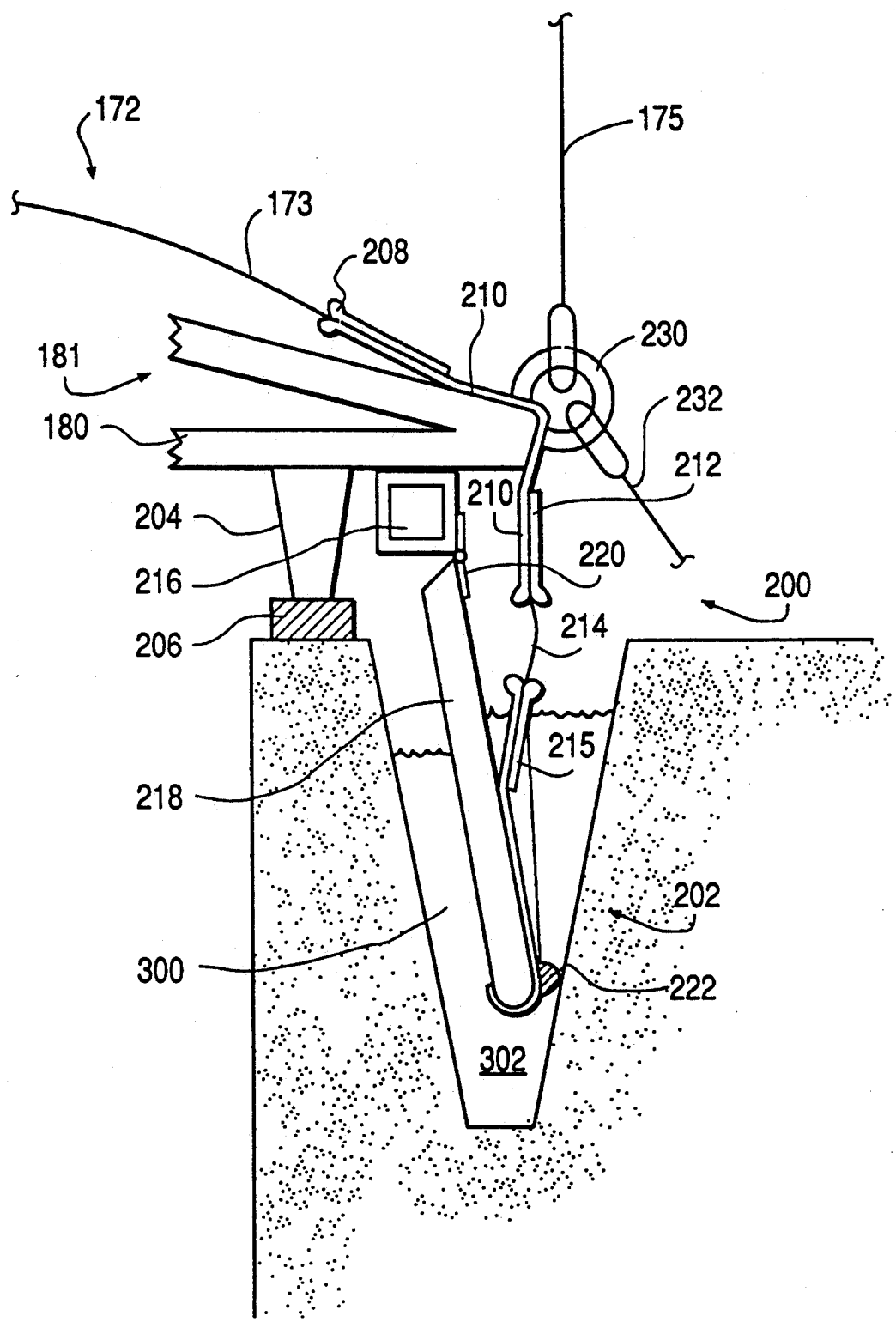
FIG. 7 is an exploded view of a water seal employed around a periphery of the trench to hermetically seal the trench.

FIGS. 5, 6, and 7 depict further novel design features of the apparatus of the present invention. Each trench 102 is provided with a lightweight reinforced cover 172 suspended from the roof structure and ceiling portion 138 of the building 104 by a series of cable and pulley means 174 shown schematically as broken lines in FIGS. 5 and 6. The lightweight reinforced covers are employed to maintain anaerobiosis by effectively hermetically sealing the trench once it is filled with RDF. The cable and pulley means are provided to raise and lower the cover, as appropriate, at various times during the composting process.

The cover, which extends across the width of the trench and along the entire longitudinal extent of the trench, provides a convenient structure to carry a biogas or methane collection header 176, and one or more (two shown in FIG. 5) leachate sprayer pipes 178. These elements are secured to the open framework of the plurality of struts 180 comprising the cover support structure 181. The struts are not shown in FIG. 6 so that it can be more clearly shown that the methane collection header 176 and leachate sprayer pipes 178 extend in the cover along substantially the entire length of the trench.

Also shown schematically in FIG. 6 are flexible tubing elements 182, 184, which couple the header 176 and sprayer pipes 178 to fixed piping systems of the apparatus, shown schematically by boxes 186, 188 in FIG. 6. The methane collection piping system 186 can be simply a further header or collection pipe coupled to each of the trenches to collect all of the methane/biogas generated at all stages of the composting process taking place simultaneously in the plurality of the trenches 102. The fixed piping system 188 for the leachate sprayers 178 will include a plurality of pumps, leachate collection lines, and valving, interconnected between all of the trenches such that means are provided for leachate recycling between trenches, and also within the same trench, which will preferably be conducted in a manner analogous to that shown in the reactor-based system shown in FIG. 1. Toxic compound separator means 64 is also connected in with the leachate piping system so that the leachate can, as necessary, be routed through this separator 64 after it is recovered from any of the trenches. FIG. 6 also depicts schematically a leachate recovery line 190 extending from the drain system 158 underneath trench 102 to the fixed leachate piping system, whereby leachate collected in the drain system can be pumped to the leachate sprayers in either the same trench (Stage 2) or in a different trench (Stages 1 and 3).

The cover material 173 of cover 172 extending over the cover support structure 181 will be substantially impermeable to gases such as the methane generated in the anaerobic composting process and the air in the building 104 housing the trenches. The cover extends over all edges of the trench, and has a hinged skirt assembly 200 (FIG. 7) depending downwardly from the entire periphery of the cover. The hinged skirt assembly is employed in forming a water seal around the entire periphery of the trench, and the combination of the water seal and the impermeable cover material enables the collection of substantially all of the methane generated in the composting process, while at the same time sealing off the trench from the external environment to inhibit any aerobic composting activity.

The constructional details of the hinged skirt assembly 200 and water seal 202 are best seen in the cross-sectional exploded view of FIG. 7. This Figure also shows that when the cover is lowered into position, the cover is supported above the trench by a plurality of support legs 204 and rubber pads 206 extending downwardly from the horizontal struts 180 of the cover support structure 181 and a plurality of tightened tie-down cables 232. The tie-down cables are employed to prevent the lifting of the cover due to a biogas overpressure generated in the process under the cover. The edges of the flexible, impermeable cover material 172 are clamped in between two welded (or riveted, or crimped, for example) sheet metal retaining strips 208, 210. At least one of these retaining strips 210 is secured to and wraps around the edge of the cover support structure 181 where, at a lower end and in a substantially vertical orientation, another retaining strip 212 is employed with strip 210 to clamp a downwardly depending flexible and impermeable flap 214 therebetween. The flap 214 has a further sheet metal (e.g., aluminum) skirt-engaging member 215 sealingly clamped thereto and extending around the entire periphery of the cover.

Disposed peripherally outwardly of cover support legs 204, and attached to the underside of the cover support structure 181, is the hinged skirt assembly 200. The hinged skirt assembly is made up of a box-shaped tubular member 216 welded to the cover support structure, and a substantially rigid skirt 218, attached by hinge elements 220 to the tubular member 216, and depending downwardly therefrom. The skirt 218 is clipped into skirt engaging member 215, these elements having complementary mating surfaces at their lower ends. Skirt engaging member also has elastomeric bumpers 222 disposed near its lower edge and extending at regular, spaced intervals around the entire periphery of the skirt assembly 200.

Each trench has a shallow moat 300 disposed in a spaced-apart manner from the peripheral edges of the trench, and the moat 300 in the depicted embodiment completely surrounds the trench 102. The moat 300 is filled, preferably more than halfway, with water 302. The length of the skirt assembly 200 depending downwardly from cover 172 and the depth of the moat 300 are selected such that skirt 218 will extend into the water 302 for approximately one-half of its length, or on the order of six inches to two feet, when the cover 172 is completely lowered into position on top of the trench by the cable and pulley means 174.

The skirt assembly, when submerged in the water 302, creates a water seal which completes the substantially hermetic sealing of the cover over the trench. In order for any methane or other biogas present to escape from under the cover, the gas must pass through or displace the water 302, and move around the bottom of skirt 218, and further past elastomeric bumper 222. This, however, will not be possible in normal operation, as the methane header 176 extending along the length of the trench in the cover support structure will remove the gas before a pressure buildup sufficient to cause such a leak would occur. The process must be operated in the trench at a slight overpressure, which thereby precludes air intrusion, thus preventing the creation of an explosion hazard.

FIG. 7 illustrates the bottom portion of one of the hoisting cables 175 which forms part of the cable and pulley means. Hoisting cable 175 is secured to the cover 172 by an eye hook 230 attached to sheet metal strip 210. Also depicted is a tie-down cable 232 secured to eye hook 230, which can be fastened to a cleat (not shown), or the like, at ground level to hold the cover in place over the trench. A plurality of tie-down cables 232 are preferably spaced around the periphery of cover 172, and will thus be adapted to substantially prevent lifting of the cover due to gas overpressure inside the trench, and to prevent any inadvertent lifting of the cover, which would break the hermetic seal created. The cables will also operate to substantially prevent lateral displacement of the cover 172.

With the apparatus for performing sequential anaerobic batch composting having been thus described, a method employing the apparatus can now be set forth. The method described hereafter comprises the operations necessary to conduct one complete cycle of sequential batch anaerobic composting in accordance with a preferred method of the present invention.

Initially, municipal solid waste (MSW) is delivered by truck to tipping floor 110. White goods and hazardous items are removed from the MSW by front end loader and are properly discarded. The MSW is then transferred to the materials recovery facility 112 (of known construction) by a front end loader and a conveyor belt 113 (FIG. 2), and the MSW is sorted and shredded. Recyclable materials and rejects are removed from the MSW and are stored in bins 111, 115. The MSW remaining after being processed in the materials recovery facility is termed refuse-derived feed (RDF), and is enriched in biodegradable components and has a homogenous particle size. RDF is accumulated in RDF storage area 114, and forms the preferred feedstock for the sequential batch anaerobic composting method of the present invention.

The RDF is transferred by a front end loader to a designated hopper 122 at the front end of a conveyor belt 116 located adjacent to an empty anaerobic composting trench 102. The RDF is dropped into the hopper 122 which feeds the associated conveyor belt 116 running alongside the entire length of the open trench. At an appropriate distance from the hopper, the RDF is scraped off the belt by discharge plow 132 (or is alternatively dumped by a tripper), and dropped into the open trench. The discharge plow is gradually moved back along the belt as sections of the trench are filled on one side. The material (RDF) will be piled up in the side of the trench being filled to the level of the discharge device.

After the discharge plow has traveled the full length of trench 102, feeding of RDF to the trench 102 from that side is completed, and the same process is repeated using the hopper, conveyor belt and discharge plow on the other side of the trench 102. The size of the trench may preferably be designed to accommodate the volume of RDF produced in one week's time, with the trench being substantially completely filled by that volume.

Once the trench has been filled with RDF, trench cover 172 is lowered, With the downwardly depending skirt 218 becoming partially submerged in water 302 disposed in moat 300. Assuming that the initial process start up has been completed, and that steady state operation has been attained, the leachate from an active batch (Stage 3 in FIG. 1) of composting RDF in another trench is sprayed by sprayers 178 onto the RDF 400 (FIG. 6) to inoculate, heat, and buffer it, and to leach out organic acids (Stage 1 of FIG. 1). The leachate percolates through the RDF to the drain system 158 underneath the RDF pile, and the leachate is collected and pumped to, and sprayed on, an active batch where organic acids are converted to methane and carbon dioxide. In the course of pumping the leachate to a trench containing an active batch of composting RDF, the leachate is preferably routed through toxic compound separator means 64, so that heavy metals and other toxic compounds removed from the new batch of RDF by the leachate can be separated from the leachate prior to spraying the leachate on the active batch of composting RDF in the subsequent trench. The active batch as well as the new batch will thus have reduced levels of toxic compounds.

After approximately one week, anaerobic digestion will be well established and the valving (not shown) of the leachate piping system 188 is switched such that the leachate collected is pumped and sprayed directly back onto the RDF (Stage 2 of FIG. 1), which can be called internal recirculation of the leachate. It is to be noted that this leachate can also be routed through the toxic compound separator means 64 prior to reintroduction of the leachate onto the RDF, if the level of heavy metals or other toxic compounds is still relatively high. After one to two weeks of internal recirculation, the valving of the leachate piping system is again switched, such that the leachate collected from this trench (now Stage 3) is routed to another trench to start up a new batch of RDF. Again, if the levels of toxic compounds in this leachate warrant further separation processing, the leachate can be routed through separator means 64 prior to being pumped into the start-up trench. The leachate now being sprayed on this RDF is being pumped back from the startup trench containing new RDF.

After one week of operation as a Stage 3 trench providing startup assistance to a Stage 1 trench, all leachate spraying is ceased, and all of the free-flowing leachate is drained from under the RDF. Inert gas (e.g., nitrogen or carbon dioxide) is then injected into the drain system and is percolated upwardly through the composted RDF, and is collected by the methane or biogas header system 176. This offgas is monitored for methane content, which will decrease as any generated methane is flushed from the composted RDF. Once the methane content is sufficiently low such that no explosive mixtures could form, air is injected through the underdrain 158 into the trench.

After about 24 hours of aeration, the cover 172 is lifted by cable and pulley means 174, and the windrow turner 164 is lowered into the trench by hydraulic elevator 170, the material is turned, and the windrow turner is raised back out of the trench. The cover 172 is again lowered to minimize uncontrolled odor and moisture production in building 104. The batch is then further aerated for approximately two additional days.

Following this further aeration, the cover is raised and the windrow turner is again lowered into the trench. The lifting conveyor 166 is activated, and the turner moves down the length of the trench along one side, lifting up the digestate (composted RDF) and dropping it onto the lifting conveyor, which lifts and transfer the digestate onto one of the adjacent longitudinally extending conveyor belts 116, which has also been activated. The digestate is conveyed to the end of the trench area and dropped off the conveyor belt 116. The digestate piles up and will subsequently be moved by front end loader to the screening area 126. When the windrow turner has emptied the full length of one side of the trench, it turns around and travels back along the opposite side of the trench, emptying the digestate onto the longitudinal conveyor belt 116 on the opposite side of the trench. This digestate material is moved and dumped by the conveyor belt 116 just as was done with the other digestate material.

The material is then moved to the screening area, where oversize material is accumulated in a bin (not shown) and removed. The remaining digestate is transferred to the static pile area, where it will remain for about one week. Air is injected from the bottom of the piles, and the piles are advantageously used as biofilters for odor control of interior air in the building. The mature compost (digestate) is then removed from the building and transported to its next destination for use as, for example, a soil conditioner.

It is to be recognized that the apparatus of the present invention is not limited to the specific features described with respect to the foregoing preferred embodiment. FIGS. 8-11 depict alternate preferred features of the present apparatus, and many more variations or modifications will become apparent to those having ordinary skill in the art.

Figure 8:
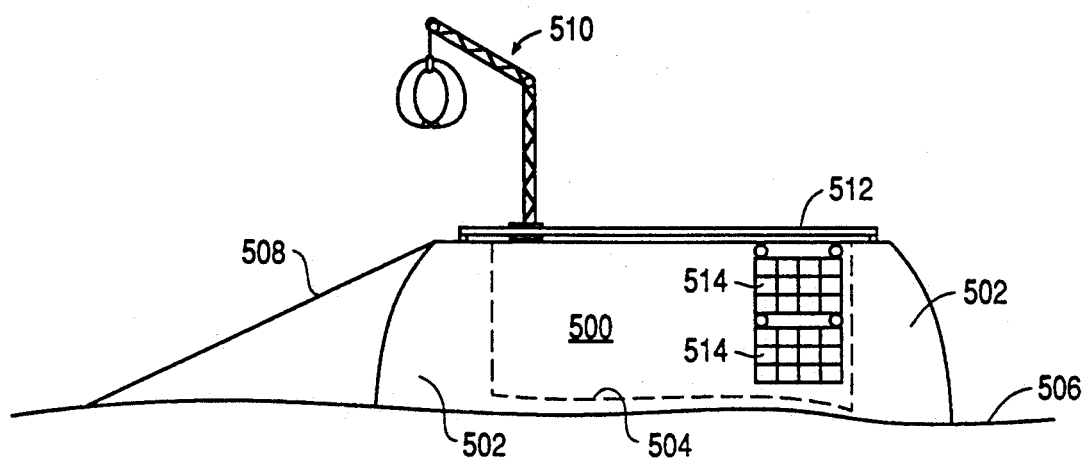
FIG. 8 is a substantially schematic cross-sectional view of a trench according to an alternative preferred embodiment of the present invention.
Figure 9:
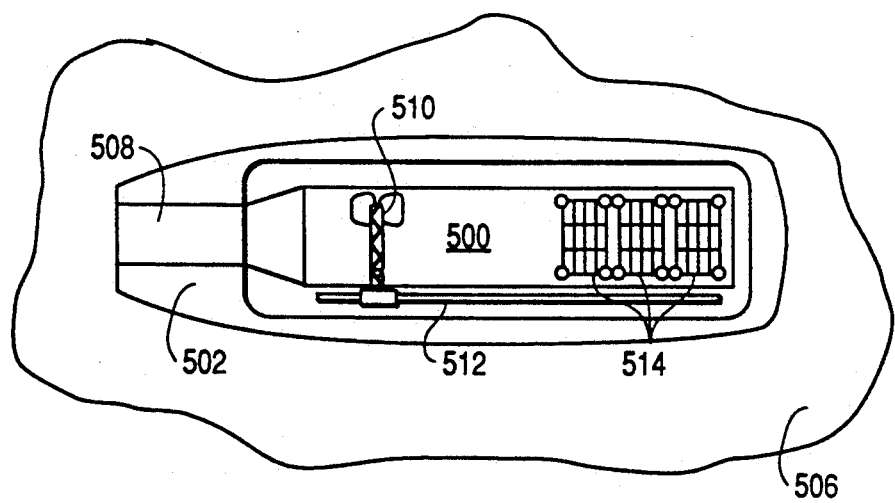
FIG. 9 is a schematic top plan view of the trench depicted in FIG. 8.

FIGS. 8 and 9 depict an embodiment for a trench 500 which may be particularly suitable for use in geographic areas where a high water table is present. A trench in such an area would preferably be built into an earthen berm or raised mound of earth 502 such that the bottom 504 of the trench remains at or near, and preferably above, the original ground level 506. The trench design and apparatus design will, in nearly all respects, be the same as those described with respect to FIGS. 2-7. There would continue to be a building housing a plurality of these bermed trenches 500, whose roof height might obviously need to be increased, and the trench would be fitted with a cover and downwardly depending skirt and water seal in a manner similar to that of FIGS. 2-7. The cover would be raised and lowered by pulleys and cables. The approach 508 to the bermed trench would preferably be graded at a shallow angle to allow dump trucks or other materials handling equipment to travel up and down to the upper level of the trench.

Also shown in FIGS. 8 and 9 is an alternative to the conveyor belt means previously discussed as a materials handling means to distribute the solid waste along the length of the trench and to collect the digested product from along the entire length of the trench. Schematically depicted in FIGS. 8 and 9 is a clamshell device means 510 of the type commonly operated by a movable crane. In the depicted embodiment, a track 512 is provided, along which the clamshell device means may travel. The propulsion means for the clamshell can be of any conventional design, and is therefore not specifically shown. As can best be seen in FIG. 9, the clamshell device 510 is designed to be able to reach substantially all portions of the trench to thereby aid in efficient filling and emptying of the trench.

FIGS. 8 and 9 further schematically depict a materials handling means which is a possible alternative to handing the solid waste in loose form. Semi-trailer sized cages 514 (or other sized cages) could be used to contain the solid waste therein, with the cages being filled with the feedstock and then being delivered to and placed in trench 500 to undergo the anaerobic digesting processing. When the process is complete, the cages 514 are removed from the trench and the treatment process is completed with the compost either in or outside of the cages. The cages could be handled by a hook assembly (not shown) either with or without lifting cables, which could replace the clamshell device 510 depicted in FIGS. 8 and 9. Alternatively, in a subterranean trench having driving ramps, it may be possible to have the cages delivered and removed directly by wheeled vehicles.

Figure 10:
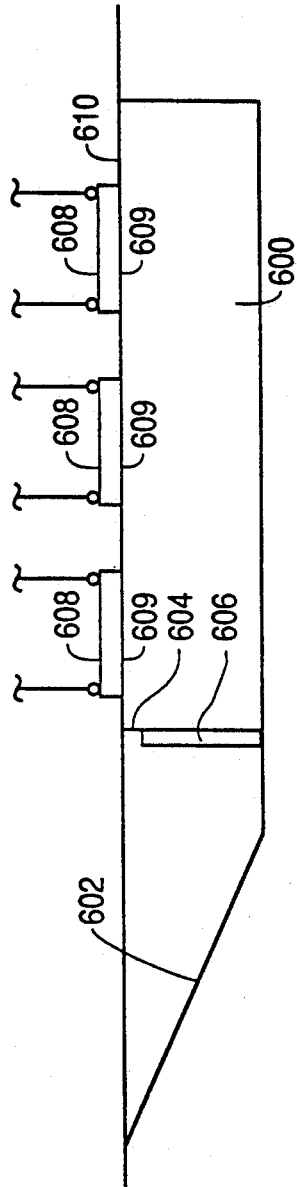
FIG. 10 is a substantially schematic cross-sectional view of a trench according to a further preferred embodiment of the present invention.
Figure 11:
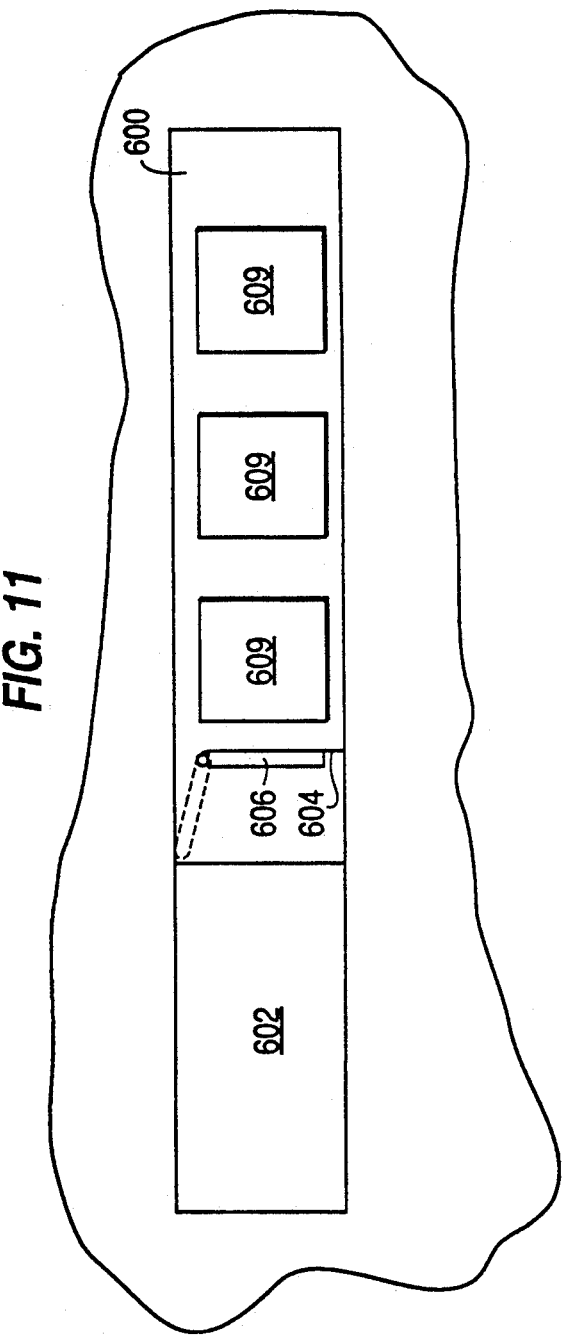
FIG. 11 is a schematic top plan view of the trench depicted in FIG. 10.

In FIGS. 10 and 11, a further trench 600 embodiment is depicted. This trench 600 is shown as being a subterranean trench having an approach ramp 602 at the outside portion of the trench, with the end wall 604 of trench 600 being provided with a bulkhead-type door 606 which is capable of being sealed in an airtight manner. This trench 600 further does not have a cover which spans the entire length and width of the trench, but instead has a plurality of smaller covers 608, fitted over openings 609 in a top ceiling 610 of trench 600. Each of the covers 608 is contemplated to be raised and lowered in substantially the same manner as has previously been described with respect to the FIG. 2-7 embodiment. Further, although the covers 608 are shown only schematically, it is intended that these covers will each have an individual water seal created by a moat surrounding each opening, with each cover having its own downwardly depending skirt.

The trench embodiment of FIGS. 10 and 11 would operate by loading the feedstock in some manner, such as dump truck or one of the other materials handling means discussed herein, through the various openings 609 in the ceiling 610 of the trench. It is to be noted that the openings will be spaced sufficiently closely such that the trench can be substantially filled using just the openings. The trench in this embodiment would preferably be emptied using front end loaders or some other vehicular materials handling equipment. The leachate spraying means and biogas collection means in this embodiment could be mounted to the ceiling instead of inside the cover, as in the embodiment shown in FIGS. 2-7.

Variations of the depicted preferred embodiments are envisioned for use with the present invention. As an example, a ramp leading from the ground level to the bottom floor of the type of trench depicted in FIG. 6 may be provided, thereby enabling trucks or front end loaders to enter and exit the trench to deposit and remove the RDF, which could prove to be an acceptable alternative to the use of the conveyor belts and discharge plows depicted, for example, in FIG. 4. The longitudinally extending trenches could be replaced by controlled reusable landfill cells, which would preferably be concrete lined or lined with some other material. The landfill cells would employ most of the features of the depicted embodiment, for example a cover providing an hermetic seal, a leachate collecting drain system, a biogas recovery system, and a leachate spraying system.

It can be seen from the foregoing description that the present invention provides a novel and economically operated commercial scale apparatus for performing a sequential batch anaerobic composting method, and a commercially viable method for anaerobic batch composting of MSW. It should be appreciated that various modifications and changes to the apparatus and method may become apparent to those skilled in the art upon reading the foregoing description, which modifications or changes do not depart from the spirit and scope of the present invention. Accordingly, the scope of the present invention is to be determined by referring to the appended claims.

What is claimed is:

1. Apparatus for the sequential batch anaerobic conversion of waste having a high-solids content to a phase comprising methane and a solid phase comprising compost, said apparatus comprising:
a plurality of waste-receiving receptacles, each of said receptacles being in contact with the ground, each of said receptacles being open over a substantial portion of an upper end thereof,
removable cover means for covering and for substantially hermetically sealing off each of said plurality of receptacles from an external environment;
means carried by said removable cover means for collecting said phase comprising methane and removing said phase from each of said plurality of receptacles;
means carried by said removable cover means for spraying a leachate onto said waste disposed in each of said plurality of receptacles;
means disposed at an underside of each of said plurality of receptacles for collecting said leachate after it has percolated through said waste; and
means for selectively transferring said collected leachate to each of said leachate spraying means in each of said plurality of receptacles.

2. Apparatus as recited in claim 1, further comprising separator means for separating toxic compounds from said collected leachate, said separator means being operatively coupled to said leachate transferring means.

3. Apparatus as recited in claim 1, wherein each of said plurality of receptacles is disposed substantially completely below ground level.

4. Apparatus as recited in claim 1, wherein each of said plurality of receptacles is disposed in an earthen berm.

5. Apparatus as recited in claim 3, wherein each of said receptacles has a water-containing moat surrounding its entire periphery at said open upper end of each receptacle, and said removable cover means has a skirt assembly attached thereto and extending downwardly therefrom, said skirt assembly being so constructed and arranged to be at least partially submerged in said water in each of said moats around an entire periphery of each of said plurality of receptacles when said removable cover means is in place on each of said receptacles.

6. Apparatus as recited in claim 4, wherein each of said receptacles has a water-containing moat surrounding its entire periphery at said open upper end of each receptacle, and said removable cover means has a skirt assembly attached thereto and extending downwardly therefrom, said skirt assembly being so constructed and arranged to be at least partially submerged in said water in each of said moats around an entire periphery of each of said plurality of receptacles when said removable cover means is in place on each of said receptacles.

7. Apparatus as recited in claim 3, wherein said removable cover means comprises a separate receptacle cover for each of said plurality of receptacles, and each of said covers has an associated skirt assembly attached thereto.

8. Apparatus as recited in claim 4, wherein said removable cover means comprises a separate receptacle cover for each of said plurality of receptacles, and each of said covers has an associated skirt assembly attached thereto.

9. Apparatus as recited in claim 7 wherein each of said receptacle covers comprises a flexible material which is substantially impervious to said phase comprising methane.

10. Apparatus as recited in claim 9 wherein each of said receptacle covers has a cover support comprising a plurality of interconnected struts having approximately the same shape as said open upper end of each of said receptacles.

11. Apparatus as recited in claim 6, wherein each of said plurality of receptacles comprises a rectangular trench having a longitudinal extent.

12. Apparatus as recited in claim 11 wherein said plurality of trenches are mutually parallel along said longitudinal extents.

13. Apparatus as recited in claim 12 wherein each of said plurality of trenches has concrete lined side walls and a concrete bottom wall.

14. Apparatus as recited in claim 13 wherein said means for collecting said leachate comprises a drain system disposed underneath said bottom wall, said drain system being in fluid communication with said portion of said trench above said bottom wall.

15. Apparatus as recited in claim 13 wherein said side walls further include an insulating layer disposed between said concrete and said ground.

16. Apparatus as recited in claim 1 wherein said plurality of receptacles are housed within an enclosed building.

17. Apparatus as recited in claim 1 wherein said leachate spraying means of each of said receptacles is operatively connected to said leachate transferring means by flexible tubing coupled to said leachate spraying means at an opening in said removable cover means.

18. Apparatus as recited in claim 1 wherein said methane phase collecting means for each of said plurality of receptacles is operatively connected to a fixed methane phase collection header means by flexible tubing connected to said methane phase collecting means at an opening in said cover means.

19. Apparatus as recited in claim 12 further comprising a plurality of conveyor belt means for transporting said waste along each longitudinally extending side of each of said plurality of trenches.

20. Apparatus as recited in claim 19 further comprising a plurality of hoppers, wherein one hopper is disposed at a front end of each of said plurality of conveyor belt means.

21. Apparatus as recited in claim 19 wherein each of said conveyor belt means has a discharge plow means associated therewith, said discharge plow means being adapted to travel along substantially the entire length of said conveyor belt means at a position immediately above an upper surface of said conveyor belt.

22. Apparatus as recited in claim 21, further comprising means for emptying said waste from each of said trenches, said emptying means comprising a lifting conveyor belt adapted to lift said waste upwardly and to discharge said waste onto a longitudinally disposed conveyor belt means extending along a side of each of said plurality of trenches.

23. Apparatus as recited in claim 1 further comprising means for loading and unloading said waste to be converted into said plurality of receptacles.

24. Apparatus as recited in claim 23 wherein said loading and unloading means comprises a clamshell device.

25. Apparatus as recited in claim 23 wherein said loading and unloading means includes a vehicle ramp permitting access to said receptacles by materials handling vehicles.

26. Apparatus as recited in claim 1 wherein each of said plurality of receptacles is a longitudinally extending trench having a plurality of openings in a top ceiling of said trench, and wherein each of said openings has removable cover means associated therewith.

27. Apparatus as recited in claim 26 further comprising a door means disposed in a side wall at one end of each of said trenches, for substantially hermetically sealing each of said trenches at said end when said door means is closed.

28. Apparatus as recited in claim 1 wherein at least four receptacles are provided.

29. Apparatus for the sequential batch anaerobic conversion of waste to a phase comprising methane and a solid phase comprising compost, said apparatus comprising:
    a plurality of horizontally extending trenches open along an upper extent thereof;
    at least one horizontally extending belt means disposed to the side of and extending parallel to each of said plurality of trenches for conveying waste from a predetermined end of said belt means along the entire length of each of said plurality of trenches;
    shifting means for shifting waste from said at least one belt means to a trench adjacent to said belt means;
    means for covering each of said plurality of trenches;
    means for substantially hermetically sealing each of said plurality of trenches;
    means for introducing a leachate onto waste disposed in each of said plurality of trenches to treat said waste;
    means for draining said leachate from each of said plurality of trenches;
    transfer means extending between each of said plurality of trenches to at least one other of said plurality of trenches for transferring said leachate drained from each of said plurality of trenches to said introducing means of said at least one other of said plurality of trenches;
    means for recovering said phase comprising methane from each of said plurality of trenches;
    extraction means for extracting said waste from each of said trenches and for delivering said waste to an adjacent horizontally extending belt means for moving said treated waste to a compost receiving area.

30. Apparatus as recited in claim 29 further comprising separator means for separating toxic compounds from said leachate, said separator means being connected with said transfer means.

31. Apparatus as recited in claim 29 wherein said plurality of open trenches extend parallel to one another, and said at least one belt means extends parallel to each of said plurality of open trenches.

32. Apparatus as defined in claim 31 wherein at least one of said plurality of trenches has a belt means on both sides thereof.

33. Apparatus as defined in claim 32 wherein said shifting means comprises means for plowing said waste into an adjacent trench, said plowing means having a plow surface which is movable along an entire axial extent of said at least one belt means immediately above an upper surface of said belt means.

34. Apparatus as defined in claim 29 comprising at least four horizontally extending open trenches.

35. Apparatus as defined in claim 34 wherein each of said at least four trenches has belt means extending along both longitudinal sides of each of said trenches.

36. Apparatus as defined in claim 29 wherein said hermetic sealing means comprises a water-containing moat extending around an entire periphery of each of said open trenches, and a hinged skirt assembly attached to and extending downwardly from said covering means, said moat being so constructed and arranged to receive said skirt assembly therein when said covering means is placed in position on each of said plurality of trenches.

37. A method for performing a three stage sequential batch anaerobic composting process for converting waste having a high solids content to a gas phase containing methane and a solid phase comprising compost, said method comprising:
    a) in a first stage:
        i) depositing a quantity of waste to be converted into one of a plurality of open receptacles disposed in contact with the ground;
        ii) then covering said receptacle with a removable, gas-impermeable cover means;
        iii) sealing said receptacle substantially hermetically with said cover means to prevent said gas phase from escaping to an external environment and to prevent said external environment from entering said covered receptacle;

iv) then initiating anaerobic digestion of said waste by inoculating said waste disposed in said sealed receptacle with a mature leachate obtained from a receptacle underoging a third state processing, said leachate containing activated culture of hydrolytic and methanogenic anaerobic microorganisms;

v) recovering said leachate after it has passed through said waste and transferring said leachate to said receptacle undergoing said third stage processing; and b) in a second stage:

i) continuing said anaerobic digestion of said waste to substantial completion to produce said gas and solid phases by continuously recirculating leachate passing through said waste back onto said waste in the same receptacle; and c) in a third stage:

i) introducing a leachate recovered from a receptacle undergoing first stage processing onto said substantially completely anaerobically digested waste;

ii) recovering said leachate after it has passed through said waste;

iii) transferring said recovered leachate to a receptacle undergoing first stage processing;

iv) discontinuing, after a predetermined amount of time, introduction of leachate into said receptacle, and draining the remaining leachate from said receptacle;

v) then aerating, turning and further aerating said solid phase comprising compost;

vi) extracting said solid phase from said receptacle; and d) in each of said first, second, and third stages in each of said plurality of receptacles, recovering said gas phase generated and transferring said gas phase to a single collection means.

38. The method of claim 37, comprising the further step of:

e) in one or more of said first, second, and third stages, separating toxic compounds from said recovered leachate.

39. The method of claim 38, wherein said toxic compounds separated from said leachate comprise heave metals.

* * * * *

UNITED STATES PATENT AND TRADEMARK OFFICE
CERTIFICATE OF CORRECTION

PATENT NO. : 5,269,634

DATED : Dec. 14, 1993

INVENTOR(S) : David P. Chynoweth, et al

It is certified that error appears in the above-identified patent and that said Letters Patent is hereby corrected as shown below:

In column 29 at line 4 (claim 37, line 20): change "underoging" to -- undergoing --; change "state" to -- stage --.

In column 30 at line 23 (claim 39, line 2): change "heave" to -- heavy --.

Signed and Sealed this

Third Day of May, 1994

BRUCE LEHMAN

Attest:

Attesting Officer

Commissioner of Patents and Trademarks